(12) United States Patent
Hiles et al.

(10) Patent No.: US 12,013,066 B1
(45) Date of Patent: Jun. 18, 2024

(54) METHODS AND SYSTEMS FOR REVERSIBLY CONSUMMATING FLUIDIC CONNECTIONS

(71) Applicant: Trisk Bio Ltd., Stevenage (GB)

(72) Inventors: Adam Luke Hiles, Leighton Buzzard (GB); Gergo Bohner, Cambridge (GB); Ryan Olf, Cambridge (GB); Samuel Isidor Jones, London (GB); Thomas Felix Martin Cummings, London (GB); Gabor Pap, Stevenage (GB); Spencer Ryan Wilson, London (GB); Aaron Garden Cantrell, Easthampton, MA (US); Michael Anthony Disimoni Stone, Holyoke, MA (US); Matthew Edwin Page, Florence, MA (US)

(73) Assignee: Trisk Bio Ltd., Stevenage (GB)

( * ) Notice: Subject to any disclaimer, the term of this patent is extended or adjusted under 35 U.S.C. 154(b) by 0 days.

(21) Appl. No.: 18/386,716

(22) Filed: Nov. 3, 2023

(51) Int. Cl.
*F16L 37/30* (2006.01)
*A61M 39/18* (2006.01)
*F16L 29/00* (2006.01)
(Continued)

(52) U.S. Cl.
CPC .............. *F16L 37/30* (2013.01); *A61M 39/18* (2013.01); *F16L 29/007* (2013.01); *F16L 37/56* (2013.01);
(Continued)

(58) Field of Classification Search
CPC ...... A61M 39/12; A61M 39/14; A61M 39/16; A61M 39/18; A61M 2039/167;
(Continued)

(56) References Cited

U.S. PATENT DOCUMENTS

| | | | | |
|---|---|---|---|---|
| 3,000,655 A | * | 9/1961 | Chilcoat | F16L 37/02 |
| | | | | 137/614.04 |
| 3,674,290 A | * | 7/1972 | McNally | F16L 47/18 |
| | | | | 285/248 |

(Continued)

FOREIGN PATENT DOCUMENTS

| | | | | |
|---|---|---|---|---|
| CA | 2292087 A1 | * | 6/2000 | F16L 39/00 |
| CN | 109578705 A | * | 4/2019 | F16L 53/70 |

(Continued)

*Primary Examiner* — Robert K Arundale
*Assistant Examiner* — Richard K. Durden
(74) *Attorney, Agent, or Firm* — Weiss & Arons LLP

(57) ABSTRACT

Provided herein is a method for sterile fluid transfer. A first array of conduits may be disposed in a first compartment having a planar face with an array of cavities, each containing a cannular protrusion fluidly connected to a conduit. A second array of conduits may be disposed in a second compartment having its own planar face with an array of surface cannular protrusions, each fluidly connected to a conduit in the second array. The method may include sterilizing the lumens of each conduit-protrusion pair; snugly juxtaposing the two planar faces to form an array of steam-tight chambers; introducing a sterilizing gas into the chambers; expelling the sterilizing gas from the chambers; moving each cannular protrusion towards its facing surface protrusion to reversibly form a fluid connection therebetween, while the chamber remains externally sealed, and transferring a fluid across at least one fluidic connection.

10 Claims, 22 Drawing Sheets

(51) Int. Cl.
  *F16L 37/56*   (2006.01)
  *F16L 53/70*   (2018.01)
  *A61L 2/07*    (2006.01)
  *B01L 3/00*    (2006.01)
  *C12M 1/00*    (2006.01)
  *C12M 1/12*    (2006.01)
  *G01N 35/10*   (2006.01)

(52) U.S. Cl.
  CPC .............. *A61L 2/07* (2013.01); *B01L 3/563* (2013.01); *C12M 1/121* (2013.01); *C12M 23/40* (2013.01); *F16L 53/70* (2018.01); *F16L 2201/44* (2013.01); *G01N 35/1074* (2013.01)

(58) Field of Classification Search
  CPC ....... A61M 2039/267; A61M 2039/268; B01L 3/563; B67C 3/2642; B67C 2003/228; B67C 7/008; F16K 1/446; F16L 29/00; F16L 29/007; F16L 33/226; F16L 37/002; F16L 37/06; F16L 37/28; F16L 37/30; F16L 37/36; F16L 37/44; F16L 37/56; F16L 37/60; F16L 53/70; F16L 2201/40; F16L 2201/44; G01N 35/1065; G01N 35/1074; Y10S 285/92; Y10T 137/4245; Y10T 137/4266; Y10T 137/87153
  USPC ...... 285/26, 124.2, 124.3, 124.4, 124.5, 248
  See application file for complete search history.

(56) References Cited

U.S. PATENT DOCUMENTS

| | | | | |
|---|---|---|---|---|
| 4,030,494 A | * | 6/1977 | Tenczar | F16L 37/02 285/21.2 |
| 4,349,508 A | * | 9/1982 | Liede | B65B 55/10 422/26 |
| 4,453,566 A | * | 6/1984 | Henderson, Jr. | F16L 39/02 137/236.1 |
| 4,497,773 A | * | 2/1985 | Kuelzow | A61L 2/07 422/26 |
| 4,694,859 A | * | 9/1987 | Smith, III | F16L 1/26 285/11 |
| 5,082,245 A | * | 1/1992 | Kast | F16L 29/02 251/149.6 |
| 5,316,347 A | * | 5/1994 | Arosio | E02F 3/3654 285/85 |
| 5,649,563 A | * | 7/1997 | Shimano | F16K 1/446 137/240 |
| 5,927,318 A | * | 7/1999 | Ishibashi | B08B 3/00 141/85 |
| 6,513,837 B2 | * | 2/2003 | Fujikawa | F16L 29/007 285/904 |
| 9,675,520 B2 | * | 6/2017 | Rogers | B01L 1/02 |
| 10,060,565 B2 | * | 8/2018 | Bishop, Jr. | F17C 1/00 |
| 2003/0040104 A1 | | 2/2003 | Barbera-Guillem | |
| 2012/0089930 A1 | | 4/2012 | Stanton, IV et al. | |
| 2015/0061282 A1 | * | 3/2015 | Faldt | A61M 39/16 285/124.5 |
| 2016/0040112 A1 | | 2/2016 | Coppeta et al. | |
| 2018/0371399 A1 | | 12/2018 | Griffin et al. | |
| 2019/0192844 A1 | * | 6/2019 | Wegener | A61L 2/10 |
| 2021/0002602 A1 | | 1/2021 | Ludlam et al. | |
| 2021/0102156 A1 | | 4/2021 | Griffin et al. | |
| 2022/0299144 A1 | * | 9/2022 | Bonnyman | A61M 39/105 |
| 2022/0326248 A1 | | 10/2022 | Miltenyi et al. | |
| 2023/0285734 A1 | * | 9/2023 | Madsen | A61M 39/16 |

FOREIGN PATENT DOCUMENTS

| | | | | |
|---|---|---|---|---|
| EP | 0230864 A1 | * | 8/1987 | ............ A61M 39/18 |
| WO | WO-2022256403 A1 | * | 12/2022 | |

\* cited by examiner

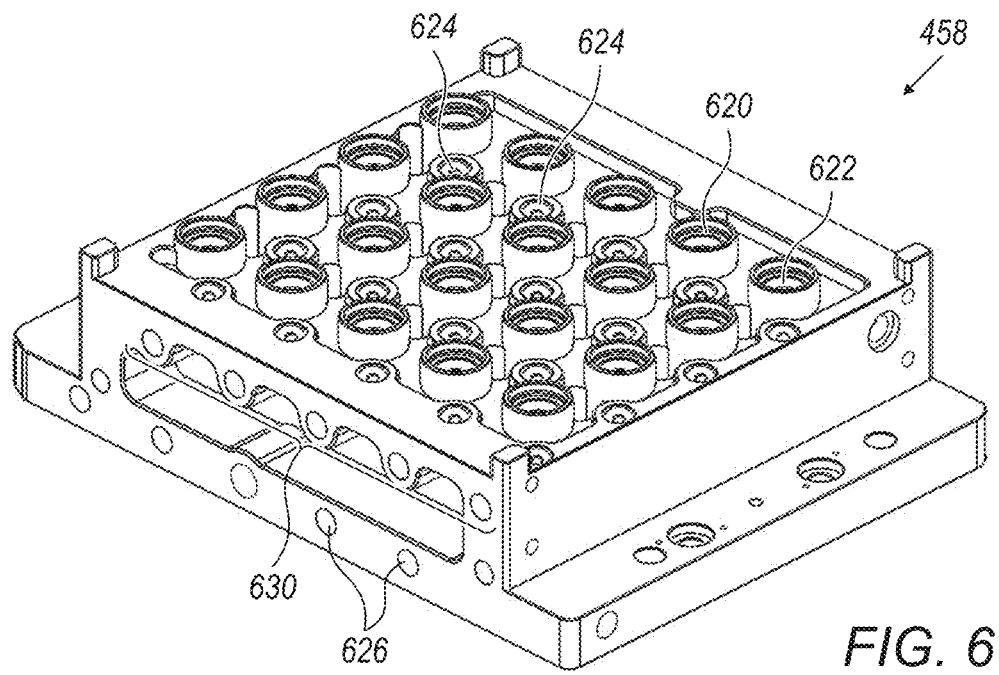
FIG. 6
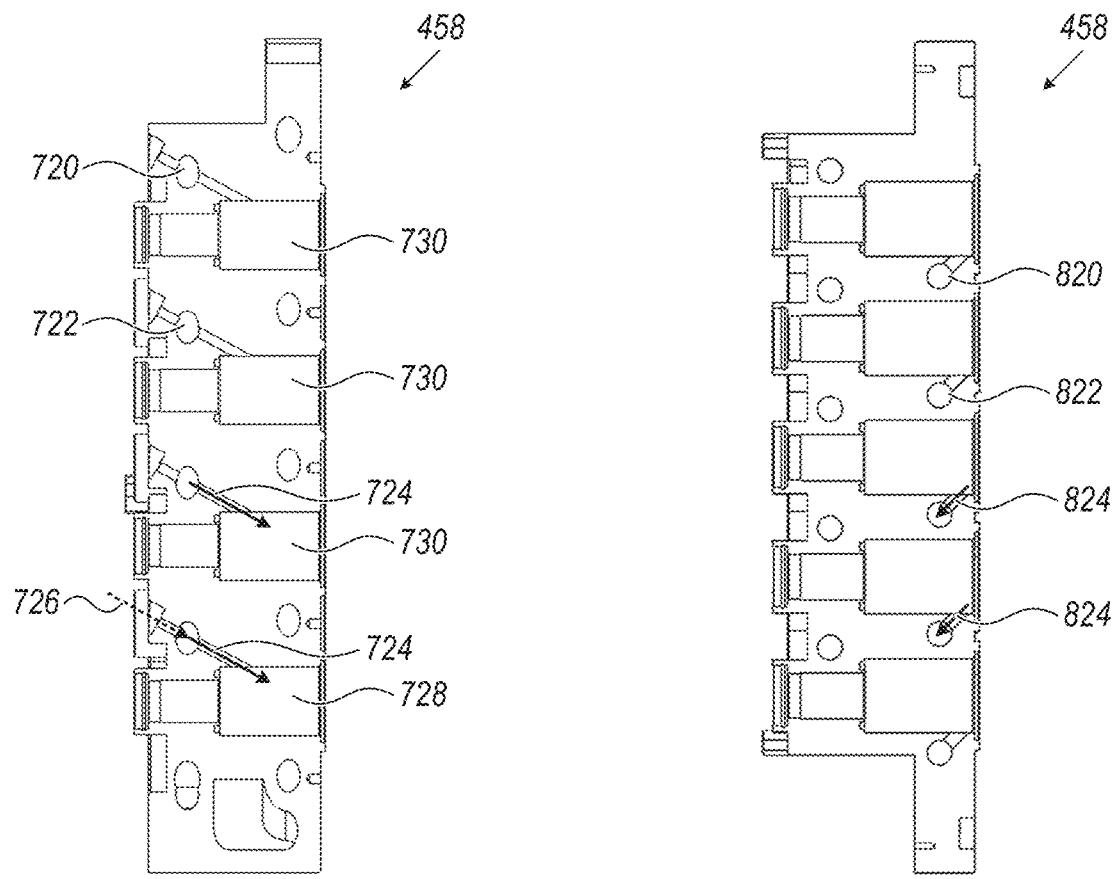
FIG. 7
FIG. 8

METHODS AND SYSTEMS FOR REVERSIBLY CONSUMMATING FLUIDIC CONNECTIONS

FIELD OF TECHNOLOGY

Aspects of the disclosure relate to methods and systems for conducting biological and biochemical processes, for example cell culture and purification of products derived from cells.

BACKGROUND

Apparatus for biological and biochemical procedures often require labor-intensive assembly and disassembly protocols. Tubes, conduits, and other components must be manually cleaned, assembled, sterilized, and leak tested at each stage, significantly contributing to labor costs, run time, complexity, and downtime between runs. Furthermore, the significant reliance on manual assembly and disassembly of connections introduces potential for human error in adherence to the specified parameters, sterilization technique, and audit trail documentation. Methods with improved efficiency, reliability, and reproducibility are urgently needed.

SUMMARY OF THE DISCLOSURE

It is an object of the present disclosure to provide a facile system architecture for sterile, reversible, and readily cleanable fluidic connections. It would be advantageous to make and detach fluidic connections between different compartments without labor-intensive procedures.

It is a further object of the present disclosure to decrease downtime between runs of apparatus for conducting biological and biochemical procedures.

It is a further object of the present disclosure to provide an apparatus for biological and/or biochemical processes that enables process modification by simple replacement of portable modules or components thereof.

It is a further object of the present disclosure to provide a system for assembling and disassembling fluidic connections that enables fully or largely automated process execution.

It is a further object of the present disclosure to reduce the footprint of biological and biochemical processes and reduce the amount of equipment required for such processes.

Aspects of the present disclosure improve upon conventional approaches by providing an apparatus for steam-sterilizable, easily cleanable, reversible liquid connections, some aspects of which can be consummated solely by exertion of a force axial to the fluid conduits. Further aspects of the apparatus can be maintained as a closed system that is accessed only via controlled interfaces. The controlled interfaces enable the system to maintain a sealed boundary between the internal flow paths and the external environment, preventing corruption of sensitive biological or biochemical samples. The interfaces may be amenable to robotic attachment and detachment.

Provided herein is a system, in accordance with principles of the disclosure. The system may include a first compartment. The system may include a second compartment. The system may include a reversibly connectable fluidic interface between the first and second compartments. The interface may be sterilizable. The system may include a first array of conduits and a second array of conduits.

The first array of conduits may include a first conduit and a second conduit.

The second array of conduits may include a third conduit and a fourth conduit.

The present disclosure encompasses embodiments wherein more than the named number of items (e.g., first, second, third, and fourth conduits; or first and second protrusions, or the like) are present. The named numbers of items are not intended to limit the disclosure.

The first compartment may include an array of cavities. The array may include a first and second cavity.

The first compartment may include a set of intracavitary cannular protrusions. The set may include a first and second intracavitary cannular protrusion. These first and second protrusions may be located within the first and second cavities, respectively. The first and second conduits may be fluidly connected to the first and second protrusions, respectively. The connections may enable flow of a fluid through a conduit and its associated protrusion.

The term "cannular" may be understood to refer to an object having a lumen. The lumen may be configured for a liquid to flow therethrough.

The term "intracavitary" may be understood to refer to a location of the named object entirely within a cavity.

The first compartment may include a substantially planar face. This face may be referred to herein as a "first face". This face may have an array of openings, including openings to each of the mentioned first and second cavities. The openings may be surface openings.

The second compartment may include an array of surface cannular protrusions. The array may include a first and second surface cannular protrusion. The mentioned third and fourth conduits may be fluidly connected to the first and second surface protrusions, respectively.

The terms "surface protrusions," "surface cannular protrusions," and the like, may be understood to refer to protrusions jutting out from a surface.

The second compartment may include a substantially planar face. This face may be referred to herein as a "second face". The mentioned first and second surface cannular protrusions may extend outwards from this face.

The second face may be configured to be pressed against the first face, thereby forming a first and second steam-tight chamber. The second face may be configured to fit snugly against the first face, thereby forming a first and second steam-tight chamber. The term "snugly" may be understood to refer to a fit of two objects to each other that forms a tight seal.

The first chamber may include the first cavity, the first intracavitary cannular protrusion, and the first surface cannular protrusion. The first chamber may encompass the first cavity, the first intracavitary protrusion, and the first surface protrusion. The second chamber may include the second cavity, the second intracavitary protrusion, and the second surface protrusion. The second chamber may encompass the second cavity, the second intracavitary protrusion, and the second surface protrusion.

Within each chamber, the intracavitary cannular protrusion and the surface cannular protrusion may axially align with one another, without these protrusions initially contacting one another. This may be true, for example, for the mentioned first and second chambers.

One or more of the chambers may include a steam inlet and a steam outlet.

In response to exerting a linear force on an intracavitary protrusion, the corresponding surface protrusion may be configured to mate therewith. The mating may establish a fluidic connection between the conduits connected to the protrusions. For example, in some of the aforementioned cases, the first and third conduits and the second and fourth conduits would be fluidically connected. One or more chambers may remain steam-tight while its fluidic connection is made.

The term reversibly may be understood to refer to a connection that can be dismantled, while preserving the structure of the mentioned conduits and their ability to be cleaned and reused in a closed system. In some embodiments, the connection is configured to exclude external contaminants. In some embodiments, the connection is a sterile connection. The terms "sterile" or "sterilely" may be understood to refer to a connection that excludes access of microbes to the interior of the mentioned lines.

As used herein, the term "compartment" may be understood to refer to a portion of an apparatus or system. In some embodiments, use of this term does not necessarily require that the referred-to portion is entirely enclosed by a barrier separating it from the outside environment. In some embodiments, the described compartment is at least partially enclosed by a barrier. In some embodiments, the compartment is entirely enclosed by a barrier. In some embodiments, the compartment need not be enclosed by a barrier.

BRIEF DESCRIPTION OF THE FIGURES

FIG. 6 depicts a cutaway view of a steam chamber block, in accordance with the principles of the described embodiments.

FIG. 7 depicts a cross-sectional, side view of a steam chamber block, in accordance with the principles of the described embodiments.

FIG. 8 depicts a cross-sectional, side view of a steam chamber block, in accordance with the principles of the described embodiments.

DETAILED DESCRIPTION

Figure 1:
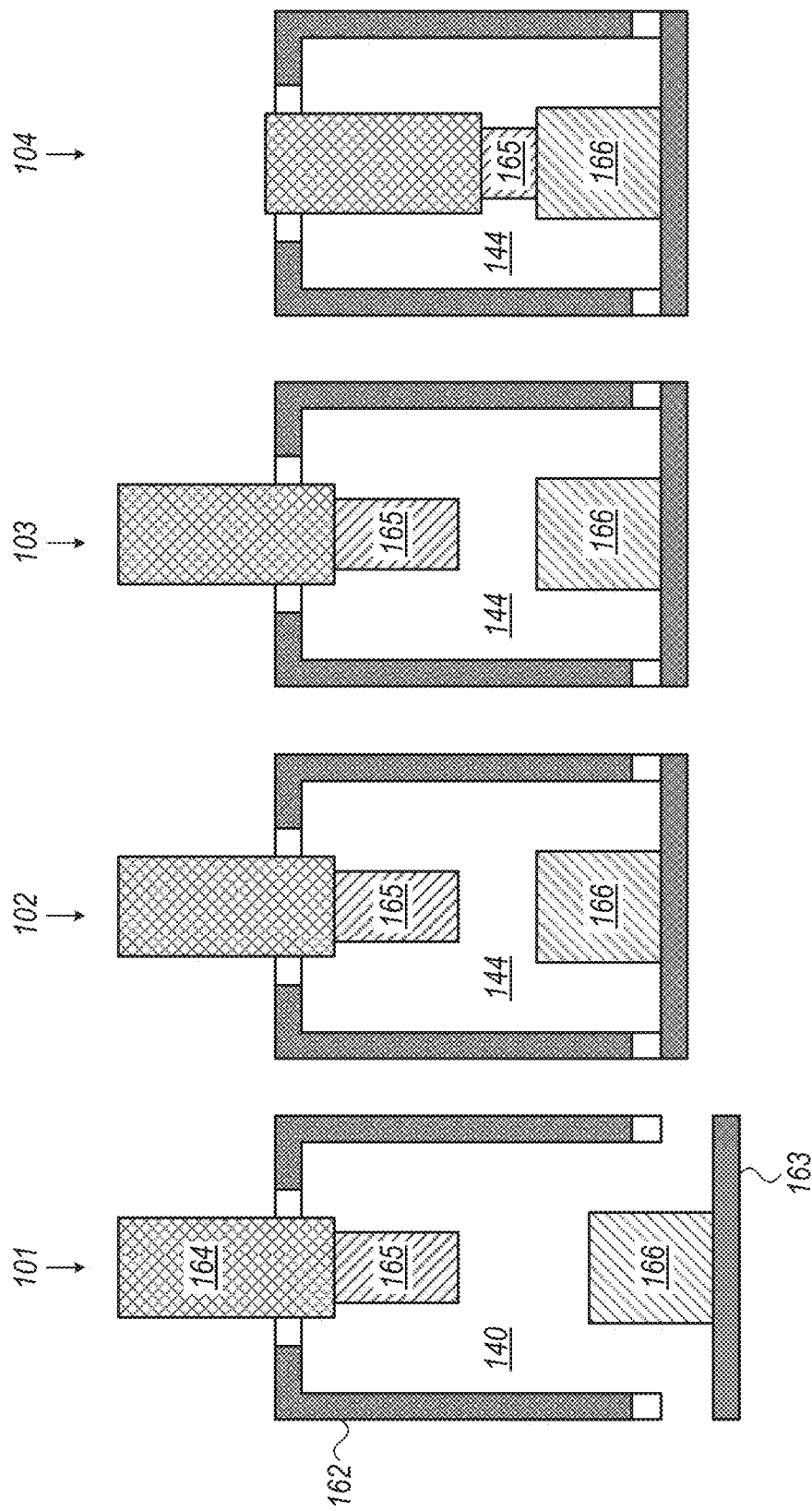
FIG. 1 is a schematic depiction of a described 4-step interface connection and sterilization process, in accordance with the principles of the described embodiments.

Provided herein is a system, in accordance with principles of the disclosure. The system may include a first compartment. The system may include a second compartment. The system may include a reversibly connectable fluidic interface between the first and second compartments. The interface may be sterilizable. The system may include a first array of conduits and a second array of conduits.

The first array of conduits may include a first conduit and a second conduit. The first array of conduits may contain more than 2 conduits.

The second array of conduits may include a third conduit and a fourth conduit. The second array of conduits may include more than 2 conduits.

The first compartment may include an array of cavities. The array may include a first and second cavity.

The first compartment may include a set of intracavitary cannular protrusions. The set may include a first and second intracavitary protrusion. These first and second protrusions may be located within the first and second cavities, respectively. The described first and second conduits may be fluidly connected to the first and second protrusions, respectively.

The first compartment may include a substantially planar face. This face may be referred to herein as a "first face". This face may have an array of openings, including openings to each of the mentioned first and second cavities. The openings may be surface openings.

The second compartment may include an array of surface cannular protrusions. The array may include a first and second surface protrusion. The mentioned third and fourth conduits may be fluidly connected to the first and second surface cannular protrusions, respectively.

The second compartment may include a substantially planar face. This face may be referred to herein as a "second face". The mentioned first and second surface cannular protrusions may extend outwards from this face.

The second face may be configured to be pressed against the first face, thereby forming a first and second steam-tight chamber. The second face may be configured to fit snugly against the first face, thereby forming a first and second steam-tight chamber.

The first chamber may include the first cavity, the first intracavitary cannular protrusion, and the first surface cannular protrusion. The first chamber may encompass the first cavity, the first intracavitary protrusion, and the first surface protrusion. The first chamber may share a common boundary with the first cavity and may encompass the first intracavitary cannular protrusion and the first surface cannular protrusion. The second face may form an additional portion of the boundary of the first chamber.

The second chamber may include the second cavity, the second intracavitary cannular protrusion, and the second surface cannular protrusion. The second chamber may encompass the second cavity, the second intracavitary protrusion, and the second surface protrusion. The second chamber may share a common boundary with the second cavity and may encompass the second intracavitary protrusion and the second surface protrusion. The second face may form an additional portion of the boundary of the second chamber.

Within one or more chambers, the intracavitary and surface cannular protrusions may axially align with one another, without the two protrusions initially contacting one another.

One or more of the chambers may include a steam inlet and a steam outlet.

In some embodiments, the mentioned second face may be configured to be pressed against the first face via application of a linear force on the second compartment.

In some embodiments, the mentioned first compartment may include a gasket.

In some embodiments, the mentioned intracavitary protrusions and surface protrusions may include auto-valved ends. In some embodiments, the intracavitary and surface protrusions both have valves on their ends that connect with each other. In some embodiments, the valves automatically shut off liquid flow when disconnected from one another.

In some embodiments, the mentioned first compartment may include a plurality of rod-shaped protrusions. The protrusions may be distributed among a plurality of edges of the first face. In some embodiments, the protruding dimension of the protrusions may be greater than the mentioned surface protrusions. In some embodiments, the second compartment may include apertures.

In some embodiments, the second compartment may include a plurality of rod-shaped protrusions. The protrusions may be distributed among a plurality of edges of the second face. In some embodiments, the protruding dimension of the protrusions may be greater than the surface cannular protrusions. In some embodiments, the first compartment may include apertures.

In some embodiments, the mentioned apertures may be equal in number to the rod-shaped protrusions. The apertures may be in corresponding positions to the protrusions. The apertures may be configured to receive, or mate with, the protrusions.

In some embodiments, the rod-shaped protrusions and the apertures may be positioned to enable alignment of the mentioned array of cavities with the array of surface protrusions. Mating of the protrusions and apertures may anchor the mentioned first and second compartments in a fixed orientation.

In some embodiments, the first compartment may include an array of internal steam channels. The mentioned steam inlets may be gaseously connected to the array. The steam inlets may be connected to the array in a manner that enables flow of steam or another gas between the inlets and the array. In some embodiments, the array may include parallel distribution lines. In some embodiments, the array may include a common steam entry point for all the steam channels.

In some embodiments, the first compartment may also include an array of additional steam channels. In some embodiments, the mentioned steam outlets may be gaseously connected to the array of additional channels. In some embodiments, the array of additional steam channels may have a common steam exit point. In some embodiments, the array of additional steam channels may include a common exit point for steam or another gas.

In some embodiments, the array of cavities may have a mirror-image geometry relative to the array of surface cannular protrusions. In some embodiments, the array of cavities may exhibit a mirror-image geometry relative to the array of surface protrusions. In some embodiments, the complementary geometry of the two arrays may enable each protrusion to fit into a cavity. In some embodiments, the complementary geometry may enable steam-tight cavities to be formed when the two compartments are pressed against one another.

In some embodiments, the array of cavities may consist of 5-30 cavities. In some embodiments, the array of cavities may contain 5-30 cavities. In some embodiments, the array of surface protrusions may contain 5-30 surface protrusions. In some embodiments, there may be equal numbers of surface protrusions and cavities.

In some embodiments, the mentioned second compartment may lack actuators. In some embodiments, the second compartment may lack sensors. In some embodiments, the second compartment may lack actuators and sensors.

In some embodiments, the mentioned surface cannular protrusions may fit into the intracavitary cannular protrusions in a plug-in-socket configuration.

Also provided herein is a method for sterile fluid transfer, in accordance with principles of the disclosure.

The fluid transfer may be between a first and second array of conduits. The first array of conduits may include a first and second conduit. The second array of conduits may include a third and fourth conduit.

The first array of conduits may be at least partially housed in a compartment. The first array of conduits may be at least partially located in a compartment. The compartment may be referred to as a "first compartment". The compartment may include a substantially planar face. The face may be referred to as a first substantially planar face or first face.

The compartment may include an array of cavities. The array may include a first and second cavity. One or more of the cavities may have an opening on the first planar face.

The first compartment may include a first intracavitary cannular protrusion located within the first cavity. The first compartment may include a second intracavitary cannular protrusion located within the second cavity.

The second array of conduits may be at least partially housed in a second compartment. The second array of conduits may be at least partially located in a second compartment. The second compartment may include a substantially planar face. The face may be referred to as a second substantially planar face or second face.

The second compartment may include an array of surface cannular protrusions. The second face may include an array of surface cannular protrusions. The array may include a first and second surface cannular protrusion.

The first and second conduits may be fluidically connected to the first and second intracavitary cannular protrusions, respectively. One or more of the conduit-protrusions pair may include a common lumen. One or more of the conduit-protrusion pairs may have a common lumen. The common lumens may be at least partially housed in the first compartment. The common lumens may be at least partially located in the first compartment.

The third and fourth conduits may be fluidically connected to the first and second surface cannular protrusions, respectively. One or more of the conduit-protrusion pairs may include a common lumen. One or more of the conduit-protrusion pairs may include a common lumen. These common lumens may be at least partially housed in the second compartment. These common lumens may be at least partially located in the second compartment.

The second face may include first and second sealing surfaces. These surfaces may surround the first and second surface cannular protrusions, respectively.

The first and second sealing surfaces may be contoured to snugly fit against the edges of the first and second cavity openings, respectively. In some embodiments, the edges of the first and second openings may be flush with the planar face. In some embodiments, the planar nature of these openings gives them a shape complementary to the first face. In some embodiments, pressing the sealing surfaces against the cavity edges produces a steam-tight seal, thus forming steam-tight chambers at the site of one or more of the cavities.

The described method may include the step of sterilizing the common lumens. The sterilized lumens may include the common lumens of both the first and second compartments.

The described method may include the step of juxtaposing the first and second planar faces. Juxtaposing the faces may form a steam-tight chamber corresponding to each cavity. For example, in some of the described cases, this action may form a first chamber, the chamber housing the mentioned first intracavitary and surface protrusions; and a second chamber, the chamber housing the mentioned second intracavitary and surface protrusions.

The described method may include the step of introducing a sterilizing gas into the chambers. For example, the gas may be introduced into the mentioned first and second chambers. The sterilizing gas may be heated. The sterilizing gas may be steam.

The described method may include the step of expelling at least 95% of the sterilizing gas from the chambers. For example, the gas may be expelled from the mentioned first and second chambers. The method may include the step of removing at least 96% of the gas. The method may include removing at least 97% of the gas. The method may include removing at least 98% of the gas. The method may include the step of removing at least 99% of the gas. The gas may be expelled from the chambers by moving pressurized air into the chambers.

The described method may include the step of moving one or more intracavitary cannular protrusions towards its corresponding surface cannular protrusion. This action may form a fluidic connection between the intracavitary and surface protrusions. This action may be performed while the chambers remain sealed. In some embodiments, each pair of intracavitary and surface protrusions is brought together individually. In some embodiments, multiple pairs of protrusions are brought together simultaneously. In some embodiments, at least two protrusion pairs are brought together simultaneously. In some embodiments, at least three protrusion pairs are brought together simultaneously. In some embodiments, at least five protrusion pairs are brought together simultaneously.

For example, in some embodiments, the described method may include moving the first intracavitary protrusion towards the first surface protrusion, thereby forming a first fluidic connection between them; and moving the second intracavitary protrusion towards the second surface protrusion, thereby forming a second fluidic connection between them.

The described method may include the step of transferring fluids across at least one fluidic connection. For example, in some embodiments, the method may include transferring a first fluid across the first fluidic connection and a second fluid across the second fluidic connection. In some embodiments, the fluid may be a liquid. In some embodiments, the fluid may be a gas. In some embodiments, the method may include transferring both a liquid and a gas. In some embodiments, the liquid and gas are transferred across the same fluidic connection. In some embodiments, the liquid and gas are transferred across different fluidic connections.

In some embodiments, the mentioned sterilizing gas may be steam. In some embodiments, the steam may be expelled from the chambers by moving pressurized air into the chambers.

In some embodiments, the described method may include the step of moving a cleaning fluid and a sterilizing fluid thorough the mentioned fluidic connections. In some embodiments, the method may include the step of detaching the first intracavitary protrusion from the first surface protrusion. In some embodiments, the method may include the step of detaching the second intracavitary protrusion from the second surface protrusion. In some embodiments, the method may include the step of detaching one or more intracavitary protrusion from its corresponding surface protrusion. In some embodiments, the aforementioned steps may be performed subsequently to the step of transferring the fluids across the fluidic connections.

Also provided herein is a fluid interface, in accordance with principles of the disclosure. Also provided herein is a system for establishing a fluid connection, in accordance with principles of the disclosure. The fluid connection may be between a first and second conduit. The first and second conduits may be at least partially located within a first and second compartment, respectively.

The mentioned first compartment may include a block. The first compartment may include a surface perforation. The perforation may open into a cavity in the block. The perforation may be the surface opening of a cavity in the block.

In some embodiments, the first compartment may include connectors or connecting pieces. Each connector may include a perforation. The perforation may open into a cavity in the connector. The perforation may be the surface opening of a cavity in the connector. The connectors may be anchored into the aforementioned block. The connectors may be slidably inserted into the block. The connectors may be welded into the block. The connectors may be otherwise anchored into the block.

The mentioned cavity may house an intracavitary cannular protrusion. The cavity may contain an intracavitary cannular protrusion. The protrusion may be fluidly connected to the mentioned first conduit.

In some embodiments, the described cavity may be in the proximal end of the connector. In some embodiments, the connector may have a substantially circular cross section. In some embodiments, the connector may have any of the components or attributes described hereinbelow.

The mentioned second compartment may contain a surface cannular protrusion protruding therefrom. The second compartment may have a surface cannular protrusion protruding therefrom. This protrusion may be fluidly connected to the mentioned second conduit.

The second compartment may be configured to be pressed against the first compartment. Doing so may form a steam-tight chamber partially bounded by the cavity. The chamber may include the intracavitary and surface protrusions. The chamber may house the intracavitary and surface protrusions. When the chamber is formed, the intracavitary and surface protrusions may axially align with one another, without contacting one another. The protrusion pair may be configured to mate with one another, in response to exerting a linear force on the intracavitary cannular protrusion. Doing so may form a fluid-tight connection between the protrusions. The process of mating the protrusions may be performable while the chamber remains externally steam tight. In some embodiments, the described system may be configured to simultaneously mate multiple pairs of intracavitary and surface protrusions. In some embodiments, the system may be configured to simultaneously mate two or more protrusion pairs. In some embodiments, the system may be configured to simultaneously mate three or more pairs of protrusions. In some embodiments, the system may be configured to simultaneously mate five or more pairs of protrusions. In some embodiments, each pair of protrusions is brought together independently.

The described cavity may be at least partially surrounded by a cooling channel connected to a liquid channel. The channel may substantially surround the cavity along its axial dimension. In some embodiments, the channel may at least substantially surround the cavity along its axial dimension. In some embodiments, the channel may substantially surround the cavity along at least the majority of its axial length. In some embodiments, the channel may at least substantially surround the cavity along at least the majority of its axial length.

The described chamber may be at least partially surrounded by a cooling channel connected to a liquid channel. The channel may substantially surround the chamber along its axial dimension. In some embodiments, the channel may at least substantially surround the chamber along its axial dimension. In some embodiments, the channel may substantially surround the chamber along at least the majority of its axial length. In some embodiments, the channel may at least substantially surround the chamber along at least the majority of its axial length.

It will be appreciated that openings in the axial length of the cavity or chamber, for example steam inlet and/or outlet openings, may partially interrupt the continuity of the cavity or channel. The present disclosure considers the cavity or chamber to be substantially surrounded by the channel in such cases. The cavity or channel may be configured to bring a cooling liquid in contact with the outer walls of the cavity or chamber.

The chamber may include a steam inlet opening. The opening may be connected to a steam channel that traverses the cooling channel.

The described interface may include a waterproof boundary between the chamber and the cooling channel. The described system may include a waterproof boundary between the chamber and the cooling channel. The described first compartment may include a waterproof boundary between the cavity and the cooling channel.

In some embodiments, the described block is a contiguous block. In some embodiments, the block may have a thermal conductivity value at 25° C. of at least 10 W/m*K (Watts per meter Kelvin). In some embodiments, the value is at least 5 W/m*K. In some embodiments, the value is between 5-450 W/m*K. In some embodiments, the value is between 10-450 W/m*K.

In some embodiments, the described cooling channel may share a common wall with the described chamber. In some embodiments, one side of the wall may be an inner surface of the cooling channel, and the other side may be an inner surface of the chamber.

In some embodiments, the described first compartment may contain a single intracavitary cannular protrusion. In some embodiments, the second compartment may contain a single surface cannular protrusion. In some embodiments, the intracavitary and surface protrusions are configured to mate with one another.

In some embodiments, the first compartment may contain two intracavitary protrusions. In some embodiments, the second compartment may contain two surface protrusions. In some embodiments, each intracavitary protrusion may be configured to mate with one surface protrusion.

Also provided herein is a method for sterile fluid transfer, in accordance with principles of the disclosure. The transfer may be between a first and second conduit. The first and second conduit may each have a lumen.

The method may include the step of juxtaposing a first compartment to a second compartment. The juxtaposing may be reversible. The method may include the step of attaching a first compartment to a second compartment. The attaching may be reversible.

The mentioned first compartment may have a planar face. The first compartment may include a planar face. The place may be referred to herein as a "first planar face." The first planar face may include an opening. The opening may lead to a cavity. The opening may be the opening of a cavity.

There may be a protrusion inside the cavity. There may be a protrusion located inside the cavity. This protrusion may be referred to herein as the "first protrusion". The first protrusion may be fluidically connected to the mentioned first conduit.

The cavity may be at least partially surrounded by a cooling channel. The cavity may be substantially surrounded by the channel along its axial dimension. In some embodiments, the cavity may be at least substantially surrounded by the channel along its axial dimension. In some embodiments, the channel may at least substantially surround the cavity along at least the majority of its axial length. In some embodiments, the channel may at least substantially surround the cavity along at least the majority of its axial length. It will be appreciated that openings in the axial length of the cavity, for example steam inlet and/or outlet openings, may partially interrupt the continuity of the channel. The present disclosure considers the cavity to be substantially surrounded by the channel in such cases. The channel may be connected to a liquid channel.

The channel may be configured to bring a cooling liquid in contact with the outer walls of the cavity. The liquid may be water. The cooling liquid may be below 25° C. The liquid may be below 20° C. The liquid may be below 15° C. The liquid may be below 10° C. The liquid may be below 5° C. The liquid may be between 0-20° C. The liquid may be between 0-15° C. The liquid may be between 0-10° C. The liquid may be between 0-5° C. The liquid may be ethylene glycol. The liquid may be between −10-+15° C. The liquid may be between −10-+10° C. The liquid may be between −10-+5° C. The liquid may be between −10-0° C.

The mentioned second compartment may have a planar face. The second compartment may include a planar face. This planar face may be referred to herein as the "second planar face". The second planar face may include a protrusion jutting out therefrom. This protrusion may be referred to herein as the "second protrusion". The second protrusion may be fluidically connected to the mentioned second conduit.

When the planar faces of the first and second compartments are juxtaposed, the second planar face may press against the mentioned opening to form an airtight chamber. Within this chamber, the first and second protrusions may be configured to not initially contact one another.

The described method may include the step of juxtaposing the planar faces of the first and second compartments. In response to performing this step, the second planar face may press against the mentioned opening to form an airtight chamber. Within this chamber, the first and second protrusions may be configured to not initially contact one another.

The described method may include the step of introducing a heated gas into the chamber via a gas channel. The gas channel may traverse the cooling channel. The heated gas may be steam.

In other embodiments, the described method may include the step of introducing a sterilizing medium into the chamber. Those skilled in the art will appreciate that a non-limiting list of sterilizing media includes steam, dry heat, ethylene oxide, vaporized hydrogen peroxide, chlorine dioxide gas, vaporized peracetic acid, and nitrogen dioxide. The sterilizing medium may be a gas, e.g., a heated gas. The sterilizing medium may be steam.

The described method may include the step of removing the gas. The method may include the step of removing at least 95% of the gas. The method may include the step of removing at least 96% of the gas. The method may include the step of removing at least 97% of the gas. The method may include the step of removing at least 98% of the gas. The method may include the step of removing at least 99% of the gas.

The described method may include the step of introducing a liquid into the cooling channel. The liquid may be water. The liquid may be below 25° C. The liquid may be below 20° C. The liquid may be below 15° C. The liquid may be below 10° C. The liquid may be below 5° C. The liquid may be between 0-20° C. The liquid may be between 0-15° C. The liquid may be between 0-10° C. The liquid may be between 0-5° C. The liquid may be ethylene glycol. The liquid may be between −10-+15° C. The liquid may be between −10-+10° C. The liquid may be between −10-+5° C. The liquid may be between −10-0° C.

The described method may include the step of exerting a linear force on the first protrusion. The method may include the step of exerting an axial force on the first protrusion. The force may move the first protrusion towards the second protrusion. The first and second protrusions may contact one another. The force may form a fluidic connection between the first and second protrusions. The contact may form a fluidic connection between the first and second protrusions.

The described method may include the step of moving a fluid between the lumens of the first and second conduits. The method may include the step of transferring a fluid between the lumens of the first and second conduits. The method may include the step of transferring a fluid between the first and second conduits.

In some embodiments, the described second protrusion may be surrounded by a sealing surface. In some embodiments, the sealing surface may press against the opening to form the airtight chamber.

In some embodiments, the described method may include the step of transferring a fluid between the described first and second conduits.

In some embodiments, the herein-described cooling channels may be between 0.5-3 millimeters, between 0.5-2 millimeters, between 0.5-1.5 millimeters, between 0.8-3 millimeters, between 0.8-2 millimeters, or between 0.8-1.5 millimeters in diameter (measured from the outer walls of the steam chamber outward). In some embodiments, the cooling channels may be in the configuration of a water jacket. In some embodiments, the cooling channels are configured to actively pump water though them, thus enabling rapid cooling of a second compartment after steam sterilization.

In some embodiments, the joining and/or sterilization process of a described interface includes some or all of the following stages or steps: Initially (disconnected mode), the two components of the chamber enclosure are disconnected. In the first stage (chamber connected mode) the two chamber enclosure components are rigidly juxtaposed, thereby forming an airtight chamber seal. In some embodiments, this is accomplished by an impetus resulting from activation of a linear (force) actuator, e.g., a component configured to transmit a linear force, or, in other embodiments, an axial force. The two conduit ends remain detached in this step. In the second stage (sterilization), steam or another sterilizing gas is brought into the chamber. In some embodiments, this is accomplished via steam routing channels, which may be disposed in a manifold block (see FIG. 9). This sterilizes the chamber (s). In the third stage (fluidic connected mode), the two conduit ends are juxtaposed. In some embodiments, this is caused by further action of the actuator. In some embodiments, when multiple connectors are present, each connection is formed individually. In other embodiments, multiple connections are formed simultaneously. In some embodiments, after the steam sterilization step, the ends are maintained in a sterile environment until after the fluid connection is consummated. In some embodiments, a sterile environment is maintained until the conduit ends are disconnected. A sterile environment refers to an environment that has been sterilized and is kept within an airtight enclosure.

In some embodiments of the herein-described systems, fluid interfaces, and methods, the cavity housing the intra-cavitary protrusion may be located in the proximal end of a body. The body may be referred to as a connector. The interface may contain one connector or body for each cavity.

In the case of the described first and second cavities, the connectors or bodies containing the first and second cavity may be referred to as the first and second connector or body, respectively. In some embodiments, the connector(s) may have a substantially circular cross section. In some embodiments, the connector(s) may be substantially cylindrical. In some embodiments, the connector(s) may have an oblong shape. In some embodiments, the connector(s) may have a shape similar to FIG. 19.

In some embodiments, the connector(s) may include a distal end. The distal end may be tapered. The distal end may be a tapered end of a substantially cylindrical shape connector (See FIG. 19).

The distal end of one or more connectors may have a depression. The distal end may have a surface cavity. The surface cavity may be referred to as a connector surface cavity, to differentiate it from the aforementioned cavity/cavities in the first compartment (which cavity/cavities contain the intracavitary protrusion[s]). The depression or surface cavity may be substantially circular. When a first and second connector is present, each connector may have a depression, which may be referred to as the first and second depressions, respectively.

In some embodiments, the described first compartment-side conduits may include a flange on one end. These conduits may include a flange on at least one end. When more than one first compartment-side conduit is present, each may include a flange. In the case of the described first and second conduits, their flanges may be referred to as first and second flanges, respectively.

The flanges of each conduit may be configured to fit into the depression of its connector. For example, in the case of the first and second conduits, their flanges may be configured to fit into the depressions of the first and second connectors, respectively. The flanges may have a substantially circular end surface (see FIG. 19). The circular end may have a diameter that is slightly less than the diameter of the depression in the corresponding connector. Slightly less, in this context, may refer to a diameter that is 0.5-2 millimeters (mm) less than the diameter of the depression.

In some embodiments, the described systems and interfaces may include a rigid, perforated disk. The disk may be referred to as a washer. The disk may be referred to as a locating washer. One or more disks may be configured to fit into the described depression of a connector. The washer may be used to align the internal bore or lumen of the conduit with a hole in the depression. The hole may lead to the described cavity in the connector. There may be a disk or washer for each flanged tube or conduit. In the case of the described first and second conduits, their disks or washers may be referred to as first and second disks or washers, respectively.

The perforation in the disk or washer may be slightly greater than the diameter of the tube or conduit whose flange inserts into the depression. Slightly greater, in this context, may refer to a number that is at most 0.4 mm greater than the diameter of the tube or conduit.

The outer diameter of the disk or washer may be slightly less than the diameter of the depression in the corresponding connector. Slightly less, in this context, may refer to a diameter that is at most 0.4 mm less than the diameter of the depression.

The disk or washer, flange, and depression associated with one or more connectors may be configured such that the flange can be inserted into the depression and overlaid with the disk or washer. The depth of the depression may be slightly less than the combined thickness of the flange wall and the washer. The depth may be substantially equal to the combined thickness of the flange wall, when compressed between 10-30%, and the washer. Substantially equal, in this context, may refer to a number that is within 0.5 mm of the combined thickness. The thickness of the flange wall may be estimable based on the thickness of the conduit wall. In some embodiments, the flange wall may have substantially the same thickness as the conduit wall.

The flange may be composed of a compressible material. The material may tolerate compression of 10-30% without undergoing plastic deformation. The term "plastic deformation" may refer to permanent plastic deformation. The term "plastic deformation" may refer to excessive plastic deformation. The washer may be composed of a substantially non-compressible material.

In some embodiments, the described systems and interfaces may include a retaining piece. There may be a retaining piece for one or more connectors. For example, in the case of the described first and second connector, their retaining pieces may be referred to as first and second retaining piece, respectively. The retaining pieces may be substantially cylindrical. The retaining pieces may have a geometry similar to FIG. 19.

The proximal end may include an aperture. The aperture may be substantially cylindrical. The axis of the cylinder may be parallel to the axis of the substantially cylindrical retaining piece. The aperture may be contoured so as to fit snugly over a tapered distal end of the described connector. The retaining piece may be configured to be attached to a tapered distal end of the connector. The attaching may utilize an external male thread on the retaining piece, which is rotated, or threaded onto a female thread on the connector. The thread may be a fine thread.

One or more of the retaining pieces may have a side aperture. The side aperture may be used to route the first compartment-side conduits out of the distal end of the connectors. The route may be similar to that depicted in FIG. 18.

One or more retaining pieces may include a proximal end. The proximal end may be on an axial end of the substantially cylindrical shape of the retaining piece.

The connection between the retaining piece and the connector may be reversible. The connection may be a secure connection. Attachment of the retaining piece to the connector may exert an axial pressure on a disk or washer and flanged conduit end resting within a depression on the connector. Attachment of the retaining piece to the connector, for example over the distal end of the connector, may serve to compress the flanged end of a tube or conduit resting within the depression. Compression of the flanged end may enable formation of a steam-tight seal at one end of the described cavity in the connector.

If more than one connector is present in the described systems, interfaces, and methods, any of the aforementioned characteristics may apply to each connector. If more than one retaining piece is present, any of the aforementioned characteristics may apply to each retaining piece.

In embodiments of the described methods and systems, the connectors joining the 2 sides of an interface between different compartments may be hydraulic connectors. In some embodiments, the connectors may be pneumatic couplings. The couplings may include two parts. The two parts may be the quick coupling, or the female part, and the plug-in, nipple, or male part.

The connectors may be configured to automatically shut off liquid flow when disconnected. The connectors may be spring loaded or use other technologies known in the art, for example ball bearings, to enable automatic shutoff. The connectors may be quick couplings. They may include a floating ball valve that closes automatically when the coupling ends are disconnected from one another. In some embodiments, the connections may be able to withstand at least 10 bar pressure.

In some embodiments, the connectors may be flat-face connectors. Connecting the ends may engage the movement of internal springs. Disconnecting the ends may automatically close the lumen. This mechanism may act as an automatic valve.

In some embodiments, the connectors may be no-spill, no-drip, or dry break connectors. In some embodiments, the connectors are configured to impede air ingress into the flow path during connection and disconnection. Alternatively, or in addition, the connectors are configured to impede liquid egress from the flow path during connection and disconnection.

In some embodiments, the connectors may be internally valved. In other embodiments, the connectors may be externally valved. In some embodiments, the connectors may be auto valved.

Systems and Methods for Biological and Biochemical Processes

In some embodiments, the aforementioned interfaces may be a component of an apparatus. The apparatus may be configured for performing a biological process. The apparatus may be configured for performing a biochemical purification process. The apparatus may be configured for performing both a biological process and a biochemical purification process. Embodiments of the interfaces and embodiments of the apparatus may be freely combined.

In some embodiments, the aforementioned methods of creating and using interfaces may be in the context of a process. The process may be a method of performing a biological process. The process may be a method of performing a biochemical purification process. The process may be a method of performing both a biological process and subsequently a biochemical purification process. Embodiments of the interfaces and embodiments of the processes may be freely combined.

In some embodiments, there is provided herein a system, in accordance with principles of the disclosure, including an upstream apparatus and a downstream apparatus. The upstream apparatus may be configured for biotechnological processes involving living cells. The upstream apparatus may include a feature described hereinbelow. The downstream apparatus may be configured for biochemical purification procedures. The downstream apparatus may correspond to any of the described systems for biochemical purification. The upstream and/or downstream apparatus may include any of the interface features described hereinabove.

In some embodiments, the upstream and downstream apparatuses may be within a single housing. In some embodiments, the first and second apparatuses may be enclosed in separate housings. In some embodiments, the 2 apparatuses may share utilities, for example pressure actuators, utility lines, or the like.

Also provided is a method for incubating living cells, in accordance with principles of the disclosure. Also provided is a method for biochemical fractionation, in accordance with principles of the disclosure. Also provided is a method for incubating living cells and isolating a product of the cells, in accordance with principles of the disclosure. A method of the disclosure may include the steps of incubating and lysing virus-producing cells, for example using an upstream apparatus as described herein. The method may also include the step of biochemically purifying the product, for example using a downstream apparatus as described herein.

Reference herein to fluid lines and pressure lines in the described interfaces, first or second compartments, or upstream or downstream apparatus is not intended to convey that certain lines are designated exclusively for either fluid or pressure. Individual lines connecting the first and second compartments may be dual-use lines. Whether a line is used for liquid or pressurized gas may depend on the configuration of the particular upstream process. In other embodiments, each line may be used for a liquid, a pressurized gas, or both successively a liquid and a pressurized gas (in either order), during a particular bioreactor run. In some embodiments, a pressurized gas may be used to flush out a line after passage of liquid through the line, for example in order to achieve a high transfer yield.

Upstream Apparatus and Methods

Apparatus and methods for performing biological processes may be referred to herein as "upstream" apparatus and methods. In some embodiments, a bioreactor may be populated with cells, which grow and divide under controlled conditions. In some embodiments, cells may be used to produce a molecule of interest or other product, e.g., recombinant virus particles. The bioreactor may be stirred and may contain sensors for pH, dissolved oxygen, and temperature, which are used to trigger additions of acid, base, air, carbon dioxide, and warming, to maintain optimum cell health in culture. These additions may be performed using pressurized air-driven flow, as described herein.

An upstream apparatus in accordance with principles of the disclosure may include a first compartment or component and a second compartment or component. The first compartment may include, and/or be at least partially bounded by, an interface, which may be referred to as a first-side interface, via which the first and second compartments interact with each other. The apparatus may be configured for cell culture. The cell culture may be for the purpose of virus production. The cell culture may be for the purpose of cell harvesting. The apparatus may be configured for other biotechnological processes known to those skilled in the art.

The first compartment may also include: (i) one or more pressure actuators; (ii) multiple outgoing pressure lines connecting the one or more pressure actuators to the first-side interface; (iii) a bioreactor chamber; and (iv) a plurality of incoming fluid lines connecting the first-side interface to the bioreactor chamber. The bioreactor chamber may be configured to house the living cells and a growth medium.

The second compartment may include: (i) multiple fluid storage containers; (ii) multiple incoming pressure lines; and (iii) multiple outgoing fluid lines. One or more of the fluid storage containers may operably connected to at least one incoming pressure line and at least one outgoing fluid line, which means, in some embodiments, that an incoming pressure line can be used to exert pressure on the interior of the fluid storage container to which it is connected, and an outgoing fluid line can be used to convey fluid out of the fluid storage container to which it is connected. When connected, an impetus originating from the pressure actuator(s) (which may be conveyed by pressure) may serve to move fluid (e.g., buffers and other fluids required for cell incubation, cell suspensions, a virus inoculum, and the like) from reagent tanks or container in the second compartments into the bioreactor chamber. The amounts of reagents moved may be predetermined according to a set program. Non-limiting examples of fluids that may be present in the fluid storage contains are buffers (e.g., bicarbonate), anti-foaming agents, and other fluids required for cell incubation; a cell suspension, a virus inoculum, a lysis reagent, and a nuclease (non-limiting examples of which are endonucleases sold under the trade name Benzonase®). The amounts of reagents moved may be predetermined according to a set program.

In some embodiments, the first compartment may include filters that are configured to deliver a sterile gas (e.g., air) in pressurized form through one of 2-3 interfaces into tanks. The pressure may impel fluid to flow from the tanks into the bioreactor. In additional embodiments, the first compartment may be configured to reverse the air flow for sampling from the bioreactor. The first compartment may supply air through sterile filters into the bioreactor, moving fluid from the reactor across one of the interfaces and into a sample tank disposed in a described second compartment. In some embodiments, the first compartment may be configured to support steaming, monitoring, and testing of any of the herein-described components. In some embodiments, use of a pressurized gas reduces mechanical failure modes.

In some embodiments, the described pressure actuator(s) may be pressure regulator(s). In some embodiments, a pressure regulator is used as a pressure source in the described methods. The pressure regulator may be programmatically set to a predetermined pressure level by a controller. If the set pressure level is greater than the pressure in a proximal air line, which is disposed downstream relative to the actuator, pressured air may flow through the proximal air line. The filter may be operably connected to a vent, a drain, a pressure sensor, and a temperature sensor. In some embodiments, pressurized air proceeds through a sterile air line downstream of the filter to a headspace of a reagent container, which may be, in some embodiments, a medium reservoir or a reservoir of another liquid reagent (e.g., a reagent needed for a biotechnological process). In some embodiments, increased pressure in the headspace impels an amount, which may be predetermined amount, of the container's fluid contents out of the container, through a downstream fluid line, and into a fluid destination container.

In some embodiments, the outgoing pressure lines lead from the pressure actuators to the interface and are configured to transmit pressure from the pressure actuators to their termini in the first-side interface. To this end, the pressure actuator(s) may be operably connected with the outgoing pressure lines.

In some embodiments, the incoming fluid lines lead from the interface to the bioreactor chamber and are configured to transport fluid originating in fluid storage containers from the first-side interface to the bioreactor chamber.

In some embodiments, the first compartment may be configured for cleaning, sterilization and reuse. For example, it may be possible to clean sterilize the first compartment (e.g., as described herein) and subsequently use it for additional incubations.

One or more of the incoming pressure lines may be configured to sterilely and reversibly connect to one of the outgoing pressure lines. In some embodiments, the connection is via a described interface. In some embodiments, the apparatus is configured for connection and disconnection of interfaces to be largely, or fully, automated.

The first compartment may include a combination of sensors and/or valves. The sensors may include scales that serve as fluid sensors. The fluid sensors may be configured to monitor fluid transfers within the system. In some embodiments, the valves may be associated with any of the described fluid lines; for example, the incoming fluid lines. In some embodiments, the valves may be configured to prevent retrograde movement of fluid within the system. The first compartment may include at least one mass sensor. One or more mass sensors may be configured to weigh a bioreactor associated therewith. In some embodiments, a processing unit may be operably connected to the fluid sensors. In some embodiments, a processing unit may be operably connected to the mass sensor. The processing unit may be configured to generate, or create, an audit trail. The audit trail may include a record of the sequence and timing of fluid transfers within the system.

The bioreactor chamber may be made of stainless steel and may, in some embodiments, be reusable. The bioreactor chamber may be made of glass and may, in some embodiments, be reusable. In some embodiments, the bioreactor chamber may be made of plastic and may, in some embodiments, be disposable. In some embodiments, the bioreactor chamber may be made of plastic and may, in some embodiments, be reusable.

In some embodiments, each of the outgoing pressure lines and incoming fluid lines includes a terminus, collectively referred to as first-side termini. The first-side termini may be arranged in a first substantially planar array, which is, in some embodiments, disposed in the first-side interface. The first-side interface may be configured to mate with, or be juxtaposed to, a second-side interface having a corresponding spatial arrangement, e.g., a mirror image of the first-side interface.

In some embodiments, each of the incoming pressure lines and outgoing fluid lines includes a terminus, collectively referred to as second-side termini. The second-side termini may be arranged in a second substantially planar array, which is, in some embodiments, disposed in a second-side interface. The second-side interface may be configured to mate with, or be juxtaposed to, the first-side interface.

Each of the first-side termini may be configured to mate, or connect, with a corresponding second-side terminus. The interface or connector may be configured to consummate the connection in a multi-step process, for example, including the steps of (a) enclosing the termini within an enclosure resistant to pathogen entry; (b) sterilizing the interior of the enclosure; and (c) fluidly connecting the termini pairs. Sterility of the enclosure may be maintained until step (c) is completed. Step (a) may be preceded by juxtaposing (but not yet fluidly connecting) the corresponding terminus pairs. In some embodiments, each enclosure contains individual pairs of termini. In some embodiments, an enclosure encompasses multiple pairs of termini.

The first compartment may be connected to one or more utility lines or conduits which contain or supply air, a sterilizing medium (e.g., a sterilizing gas) and/or a cleaning medium (e.g., a cleaning fluid). The first compartment may be connected to additional lines which contain or supply additional compartments, for example water, diluting buffers, etc. In certain embodiments, the additional lines supply 2 or more components selected from ambient air, carbon dioxide, steam, purified water, and cleaning solution. In some embodiments, the connection is a fixed connection. Fixed may refer to a connection not intended to be disassembled and assembled on an ongoing basis, as will be appreciated by those skilled in the art.

The cleaning medium may be a cleaning fluid. The cleaning fluid may include detergents or surfactants (for example, anionic detergents or cationic detergents). Solutions of acids (e.g., citric acid, hydrochloric acid, or acetic acid) or bases (e.g., NaOH) may also be used as cleaning solutions.

In some embodiments, the second compartment (or an additional second compartment, if more than one is utilized) also includes a virus container, a third incoming pressure line connected to the virus container, and a third outgoing fluid line connected to the virus container. In other embodiments, a polynucleotide container, containing a polynucleotide solution, is present instead of a virus container. In other embodiments, a polynucleotide container, containing a polynucleotide solution, is present in addition to a virus container, either in the same second compartment (e.g., in different containers) or in a different second compartment. A corresponding outgoing pressure line(s) and an incoming fluid line(s) may be present in the first compartment and configured to mate with the virus and/or polynucleotide container-associated lines. In some embodiments, the polynucleotide is a vector required for the desired biotechnological process.

In some embodiments, the pressurized gas used in the upstream apparatus is a biologically compatible gas, for example nitrogen, oxygen, carbon dioxide, or a mixture thereof. In some embodiments, the pressurized gas is ambient air. In some embodiments, the pressurized gas is sterile filtered, for example sterile-filtered air. In some embodiments, the filters have been sterilized (e.g., via steam), and filter integrity has been tested, prior to commencing the described method.

In some embodiments, the filters impel air through one of 1-3 interfaces into reagent containers or tanks, which in turn drives fluid to flow into the bioreactor. In some embodiments, the sampling process uses a reverse air flow path. Air may be supplied through sterile filters into the bioreactor, moving fluid from the reactor across one of the interfaces and into a sample tank.

In some embodiments, a method for incubating cells may include the step of monitoring the mass of the bioreactor, combined with the contents therein. The bioreactor may be connected to a mass-measurement device (which may be, e.g., a scale or the like) to continuously or periodically monitor the mass inside the bioreactor (which can be calculated by subtracting the combined mass of the bioreactor with its contents, minus the known mass of the empty bioreactor). In some embodiments, tracking the bioreactor mass is used to monitor flow rates of solutions and samples into and out of (respectively) the bioreactor. In some embodiments, this information is used to ensure a desired combined biomass and solution volume inside the bioreactor.

In some embodiments, readings from pH, dissolved oxygen, temperature sensors in the bioreactor are transmitted to a processor. Based on this information, the processor may control additions of acidic or basic additives, oxygen, and/or carbon dioxide; heating, and stirring, to maintain cell health in the culture. These additions may be driven using pressurized air-driven flow, as described.

In some embodiments, the second compartment (which may be the described "slow" addition module) contains tanks holding liquid supplies to be added to the bioreactor, in a manner that maintains the sterility of the steam sterilized first compartment.

In some embodiments, an additional second compartment or module (which may be referred to as a "fast addition" module) constitutes a mechanism for attaching smaller modules in order to make relatively quick and small volume additions to the bioreactor. In some embodiments, the fast module is configured to allow small modules to be attached and removed more quickly than the slow module. In some embodiments, the additional second compartment is configured to be steam sterilized and water cooled, for example as described herein, to speed up the connection process. The second additional compartment may be used for reagents or components that are relatively labile.

In some embodiments, a described method also includes an additional step of moving some or all of the contents of the bioreactor chamber to a downstream container via exertion of differential pressure on the bioreactor chamber. The sample may be conveyed via a product sampling line, which may connect or lead from the bioreactor chamber to the downstream container.

In some embodiments, the downstream container may be in the aforementioned downstream apparatus. The downstream container may be a container configured to be connected to a second compartment of the downstream apparatus. In some embodiments, direct transport of the product to a container within the first compartment, or a similarly equipped compartment, enables seamless transition to downstream processing of the product.

The described upstream apparatus steps may be preceded by the following prior steps pre-a1 and pre-a2, which may be performed in either order or simultaneously: Step pre-A1: sterilely connecting the first and second outgoing pressure lines to the first and second incoming pressure lines (e.g., respectively); and Step pre-A2: sterilely connecting the first and second outgoing fluid lines to the first and second incoming fluid lines (e.g., respectively). In some embodiments, steps pre-A1 and pre-A2 are performed robotically. In some embodiments, steps pre-A1 and pre-A2 may involve a reversible connection.

Additional embodiments of upstream apparatus and methods are described in co-pending application Ser. No. 18/215,393, which is incorporated herein by reference.

Downstream Apparatus and Methods

Apparatus and methods for performing biochemical fractionation protocols or other processes may be referred to herein as "downstream" apparatus and methods.

A downstream system may include a first compartment and a second compartment. The second compartment may be reversibly connected to the first compartment. The second compartment may be reversibly connectable to the first compartment.

A downstream system may include sample containers, also referred to herein as "tank(s)", to facilitate various stages of a biochemical purification process. Additions to and samples to, from, and between the tanks may be performed using compressed air to actuate fluid movement. The air may pressurize the internal space of a liquid-containing tank and induce liquid flow out of the tank into a destination container (e.g., a filtration or chromatography apparatus or another sample container). These processes may be automated.

The air may be sterilized. Air used for transferring liquids in this way can be sterilized by passage through sterile filters, in some cases prior to reaching the sample tank. These filters themselves may be steam sterilized and tested for filter integrity via automated processes.

The system may be suitable for processing a liquid sample. The system may be suitable for performing a biochemical purification protocol. The protocol may be a virus capsid purification protocol. The protocol may be another biochemical fractionation protocol.

The first compartment of the downstream system may include an interface side. The interface side may include at least 4 orifices. The interface side may include a first orifice, a second orifice, a third orifice, and a fourth orifice. The interface side may include at least a first orifice, a second orifice, a third orifice, and a fourth orifice.

The first compartment may include a pressure actuator. The pressure actuator may be the first pressure actuator among a plurality of pressure actuators. The pressure actuator may be the only pressure actuator in the system. The term "first pressure actuator" is not intended to require the presence of additional pressure actuators in the system.

The first compartment may include at least 2 sample containers.

The first compartment may include a gas conduit. The conduit may be the first gas conduit among a plurality of gas conduits. The conduit may be the only gas conduit in the system. The first gas conduit may connect the first sample container to the first pressure actuator. The term "first gas conduit" is not intended to require the presence of additional gas conduits in the system.

The first compartment may include at least 2 sample conduits.

The first compartment may include at least 4 connectors. These connectors may be referred to herein as interface-side connectors.

The first compartment may include a reagent conduit.

In some embodiments, the first sample conduit may be connected to the first sample container and the first connector. In some embodiments, the second sample conduit may be connected to the second sample container and the second connector. In some embodiments, the reagent conduit may be connected to the third and fourth connectors. In some embodiments, the first, second, third, and fourth connectors are disposed in the first, second, third, and fourth orifices, respectively. In some embodiments, the connectors and orifices serve to connect the sample containers to the interface.

In some embodiments of the described systems and methods, each sample container is connected to at least one gas conduit and at least one sample conduit.

The described second compartment may include a connector manifold. The connector manifold may include at least 4 connectors. The connector manifold may include a fifth connector, a sixth connector, a seventh connector, and an eighth connector. These connectors may be referred to herein as manifold-side connectors.

The second compartment may include a fractionation moiety. The fractionation moiety may be referred to as a first fractionation moiety. In some embodiments, the term "first fractionation moiety" does not necessarily indicate the presence of a second fractionation moiety. The fractionation moiety may be reversibly connected to the fifth sixth, and seventh connectors.

The second compartment may include a reagent container. The reagent container may be reversibly connected to the eighth connector.

Reference herein to connection of a component, for example a container or fractionation moiety, to a connector, is not intended to imply a direct connection between the component and the connector. In some embodiments, a conduit may link the connector to the containers. In some embodiments, the connector may be a tube. The tube may be a polymer tube, non-limiting examples of which are polytetrafluoroethylene (PTFE), perfluoroalkoxy alkanes (PFA), fluorinated ethylene propylene (FEP), and nylons (linear polyamides). The tube may be stainless steel. The conduit may be directly and reversibly connected to the connector.

In some embodiments, the first connector may be connected to the fifth connector. In some embodiments, the second and sixth connectors may be connected. In some embodiments, the third and seventh connectors may be connected. In some embodiments, the fourth and eighth connectors may be connected. The connectivity may be similar to FIG. 24.

The described system may be configured to route the liquid sample from the first sample container to the fractionation moiety, and from the fractionation moiety to the second sample container. The described system may be configured to route a reagent from the reagent container to the fractionation moiety. In some embodiments, the aforementioned steps need not be the only process steps in a biochemical purification protocol. In some embodiments, the aforementioned steps may be preceded by additional steps. In some embodiments, the steps may be preceded by the step of transferring the sample to the first sample container. In some embodiments, the aforementioned steps may be followed by additional steps. In some embodiments, the steps may be both preceded and followed by additional steps.

In some embodiments, the first compartment of the described system may include a third sample container. The first compartment may optionally include a second pressure actuator.

The first compartment may include a second gas conduit. The second gas conduit may connect the second sample container to a pressure actuator. The actuator may be the first pressure actuator. The actuator may be the (optionally present) second pressure actuator. The actuator may be selected from the group consisting of the first pressure actuator and the second pressure actuator.

The described system may include at least 2 mass sensors. One or more of the mass sensors may be configured to weigh a sample container associated therewith. The system may include a first mass sensor and a second mass sensor. The first and second mass sensors may be configured to weigh the first and second sample containers, respectively.

In some embodiments, a pulseless pump may be present in the described first compartment. In some embodiments, an inline degasser may be present. In some embodiments, the described system is configured to provide a hypobaric pressure environment to one or more sample containers. Such an environment can enable degassing of the sample, e.g., before loading it onto a chromatography column.

Also provided herein is a method, in accordance with principles of the disclosure. The method may be a method for processing a liquid sample. The method may be a method for performing a biochemical purification protocol. The protocol may be a virus capsid purification protocol. The protocol may be another biochemical fractionation protocol. The protocol may be for processing a biological sample. The method may be automated.

The method may utilize an apparatus, the apparatus including a first compartment and a second compartment.

The first compartment may include an interface side. The first compartment may include at least 3 sample containers. The first compartment may include first, second, and third sample containers.

The second compartment may include a connector manifold.

The method may include the step of reversibly connecting a reagent container, a filtration apparatus, and a chromatography apparatus to the connector manifold. In some embodiments, the filtration apparatus may include a first (initial) end and a second (subsequently used) end. In some embodiments, the chromatography apparatus may include a first (initial) end and a second (subsequently used) end. The filtration apparatus may be a frontal-flow filtration apparatus. The filtration apparatus may be a tangential-flow filtration apparatus.

The method may include the step of reversibly connecting the interface side of the first compartment to the connector manifold.

The method may include the step of pressurizing the first sample container. The contents of the tank may be pressurized. The headspace of the tank may be pressurized. In some embodiments, the step of pressuring serves to actuate the transfer of sample or reagent.

The method may include the step of transferring at least a portion of the sample from the first sample container into the first end of the filtration apparatus. The sample may be routed via the described interface side and connector manifold.

The method may include the step of passing at least a portion of the sample through a filter. The filter may be located within the filtration apparatus. The filter may be located between the first and second ends of the filtration apparatus.

The method may include the step of transferring at least a portion of the sample from the filtration apparatus into the second sample container. The sample may be transferred from the second end of the filtration apparatus into the second sample container. The sample may be routed via the connector manifold and the interface side.

The method may include the step of transferring at least a portion of the sample from the second sample container into the first end of the chromatography apparatus. The sample may be routed via the interface side and the connector manifold.

The method may include the step of transferring the reagent from the reagent container into the chromatography apparatus. The sample may be routed via the first compartment.

The reagent may be a mobile phase solvent. The reagent may be a mobile phase buffer. The reagent may be introduced into the upstream end of the chromatography apparatus, with respect to its direction of mobile phase flow.

The method may include the step of transferring at least a portion of the sample from the second end of the chromatography apparatus to the third sample container. The sample may be routed via the connector manifold and the interface side.

In some embodiments, the step of transferring the sample into the first end of the chromatography apparatus is performed at a substantially constant flow rate. In some embodiments, a pulseless pump is utilized for this purpose. In some embodiments, the method further includes the step of pressuring the third sample container, during the described transferring step into the chromatography apparatus.

In some embodiments, the method further includes the step of passing at least a portion of the sample through a sterile filter. In some embodiments, sterile filtration is the final fractionation step. In some embodiments, sterile filtration is the final purification step. In some embodiments, sterile filtration is the final process step.

In some embodiments of the described method, the first compartment may include a fourth sample container.

In some embodiments, the method includes the step of reversibly connecting a tangential flow (TFF) filtration apparatus to the connector manifold. The TFF apparatus may include a tangential filter. The TFF apparatus may be in addition to the aforementioned filtration and chromatography apparatus. In some embodiments, the method may utilize a frontal-flow filtration apparatus, a chromatography apparatus, and a TFF apparatus.

In some embodiments, the method includes the step of pressurizing the third sample container. In some embodiments, the pressurization serves to transfer at least a portion of the sample from the third sample container into the first end of the tangential filtration apparatus. The sample may be routed via the interface side and the connector manifold.

In some embodiments, the method includes the step of transferring at least a portion of the sample from the first end to the second end of the tangential filtration apparatus.

In some embodiments, the method includes the step of transferring at least a portion of the sample from the second end of the tangential filtration apparatus to the fourth sample container. The sample may be routed via the connector manifold and the interface side.

In some embodiments, the method includes the step of pressurizing the fourth sample container. In some embodiments, the pressurization serves to transfer at least a portion of the sample from the fourth sample container into the second end of the tangential filtration apparatus. The sample may be routed via the interface side and the connector manifold.

In some embodiments, the method includes the step of transferring at least a portion of the sample from the second end to the first end of the tangential filtration apparatus.

In some embodiments, the method includes the step of transferring at least a portion of the sample from the first end of the tangential filtration apparatus into the third sample container.

In some embodiments of the described systems and methods, the steps of transferring the sample between the third and fourth tanks are performed iteratively. In some embodiments, these steps are performed a predetermined number of times.

In some embodiments of the described method, the third sample container is pressurized to a first pressure, and the fourth sample container is simultaneously (while the third container is pressurized) pressurized to a second pressure. In some embodiments, the first and second pressures are both greater than ambient pressure. In some embodiments, the first and second pressures alternate between the first pressure being greater than the second pressure vs. the second pressure being greater than the first pressure. In some embodiments, this arrangement enables bidirectional passage through a filtration apparatus under hyperbaric pressure. In some embodiments, the filtration system is a tangential filtration apparatus.

In some embodiments, the described method includes the step of monitoring the mass of the first, second, third, and/or fourth sample container. Monitoring mass of sample containers may enable calculation of flow rates into and out of the containers, for example as described herein. Since the empty tank's mass is constant, the flow rate of sample into or out of a tank can be calculated by the change in the full tank's mass. The calculation may utilize a processor. In some embodiments, the method includes the step of streaming mass data about a tank to a processor. In some embodiments, the method includes the step of calculating an actual flow rate from and/or into the tank.

In some embodiments, the method includes the step of pressurizing the second sample container. In some embodiments, the headspace of the second tank is pressurized.

In some embodiments, the method includes the step of monitoring the mass of the second tank. In some embodiments, the method includes the step of streaming mass data about the second tank to a processor. In some embodiments, the method includes the steps of calculating an actual flow rate from the second tank and dynamically adjusting the headspace pressure of the second tank in order to achieve the desired flow rate.

Reference herein to a sample is intended to encompass any sample that is handled by a described process and/or in a described system, regardless of its stage of purification.

In some embodiments of the described methods and systems, the first compartment includes at least one pH sensor. In some embodiments, the pH sensor is located in a fluid path between a separation moiety and a destination product container. In some embodiments, a method includes the step of monitoring pH during a purification step.

In some embodiments, the first compartment includes at least one pressure sensor. In some embodiments, the pressure sensor is located in a fluid path between a separation moiety and a destination product container. In some embodiments, a described method includes the step of monitoring pressure during a purification step.

In some embodiments, a described downstream method includes the steps of membrane filtration-mediated clarification, diafiltration via TFF, affinity chromatography, an additional TFF, IEX chromatography, a third round of TFF, and sterile filtration. In some embodiments, the aforementioned steps are performed in the mentioned order. In some embodiments, each round of TFF serves to adapt the buffer composition and/or volume to the requirements of the next step. In some embodiments, the method is a virion purification method.

In some embodiments, IEX chromatography may serve to separate capsids containing nucleic acid from unfilled capsids. In some embodiments, this step may utilize a gradual transition from wash to elution buffer. In some embodiments, this step may utilize UV sensors to monitor the column output. In some embodiments, isocratic wash and elution steps are used to release the empty and full capsids.

In some embodiments, the third round of diafiltration via TFF replaces the buffer with one suitable for storage. In some embodiments, this diafiltration brings the product to the desired concentration.

In some embodiments, sterile filtration is achieved by passage through a sterile filter. In some embodiments, sterile filtration is followed by transfer to an external fill and finish station, which is used to dose and package the product.

As used herein, the term "connector manifold" may be understood to refer to any structure that includes multiple connectors. The manifold may have a substantially planar surface. The manifold may include a contiguous block. The interface side of the first compartment may also include a connector manifold, which may include any of these characteristics.

The term "sample container" may be understood to refer to a container that is configured to contain a liquid biological product or sample.

In some embodiments, reference herein to connectors located in, or disposed in an interface or connector manifold may indicate that the connectors are embedded in the interface or manifold. In some embodiments, the connectors may be inserted into the interface or manifold.

The term "fractionation moiety" may be understood to refer to an apparatus configured to perform a biochemical fractionation or separation procedure. The fractionation moiety may be a filtration apparatus. The moiety may be a frontal-flow filtration apparatus. The moiety may be a tangential-flow filtration apparatus. The moiety may be a chromatography apparatus. Both filtration and chromatography moieties may be present in the system. Frontal-flow filtration, tangential-flow filtration, and chromatography moieties may all be present in the system.

In some embodiments of the described systems and methods, one or more of the gas conduits may be connected to a source of pressurized gas. The gas may be air. The source may be a pressure actuator. The source may be a pressure pump. The source may be selected from the group consisting of a pressure actuator and a pressure pump. In some embodiments, the described pressure actuator(s) are pressure regulator(s). In some embodiments, a pressure regulator is used as a pressure source in the described methods. The pressure regulator may be programmatically set to a predetermined pressure level by a controller. If the set pressure level is greater than the pressure in a proximal air line, which is disposed downstream relative to the actuator, pressured air may flow through the proximal air line.

As used herein, filtration may refer to passage over a membrane that selects components on the basis of size and/or other parameters.

As used herein, chromatography may refer to passage through a substrate or column that selects components on the basis of size, affinity to column components, ionic charge, or other characteristics. Non-limiting examples of chromatography are size-exclusion chromatography, affinity chromatography, ion-exchange chromatography, and mixed-mode chromatography.

Reference herein to a "first" compartment is not intended to limit the disclosure to systems wherein the named first compartment temporally handles the sample before the named second compartment. Rather, the terms "first" and "second", for example when referring to compartments, are intended to enable separate referencing of different system compartments, without implying a particular temporal progression.

Reference herein to a "first" component, for example a first orifice, sample container, gas conduit, sample conduit, or connector, is not intended to limit the disclosure to systems wherein the named first component temporally handles the sample before the named second component. Rather, the terms "first" and "second", for example when referring to any components, are intended to serve the purpose of enabling separate referencing of different system components, without implying a particular temporal progression. These terms are not intended to limit the number of components. For example, reference to a first and second conduit within an array does not intend to limit the number of conduits within the array.

Reference herein to a "gas conduit" or "liquid conduit" is not intended to require that the conduit be designated only for movement of gas or liquid (as appropriate). In some embodiments, each conduit is suitable for both gases and liquids. In some embodiments, the disclosure encompasses systems and methods wherein a given conduit is used for both a gas and a liquid in the same process. In some embodiments, a gas, for example pressurized air, may be used to flush a line after liquid transfer, to increase transfer yield.

In some embodiments, the pressurized gas used in the described systems and methods is selected from the group consisting of ambient air, nitrogen, oxygen, helium, carbon dioxide, and a mixture thereof. In some embodiments, the gas has been filtered to remove particulate matter.

The described upstream or downstream methods may include the additional step of programming a processor to execute a predetermined, choreographed fluid transfer program, e.g., via instructing the actuator(s) to move predetermined amounts of selected fluids at predetermined time intervals. Alternatively or in addition, the processor may instruct the actuator(s) to execute fluid transfers based on predetermined milestones. For the upstream apparatus, such milestones may include a desired cell density, viral particle density, or metabolic indicator. The system may be configured to automatically detect these milestones and determine the timing of each process stage accordingly.

Additional embodiments of downstream apparatus and methods are described in co-pending application Ser. No. 18/374,098, which is incorporated herein by reference.

Structural features of the described systems may be freely combined with process steps of the described methods. The described structural features are hereby incorporated into the described methods. The described method steps are hereby incorporated into the described systems.

Apparatuses and methods described herein are illustrative. Apparatuses and methods in accordance with this disclosure will now be described in connection with the figures, which form a part hereof. The figures show illustrative features of apparatus and method steps in accordance with the principles of this disclosure. It is to be understood that other embodiments may be utilized and that structural, functional, and procedural modifications may be made without departing from the scope and spirit of the present disclosure.

The steps of methods may be performed in an order other than the order shown or described herein. Embodiments may omit steps shown or described in connection with illustrative methods. Embodiments may include steps that are neither shown nor described in connection with illustrative methods.

Illustrative method steps may be combined. For example, an illustrative method may include steps shown in connection with another illustrative method.

Apparatuses may omit features shown or described in connection with illustrative apparatuses. Embodiments may include features that are neither shown nor described in connection with the illustrative apparatus. Features of illustrative apparatus may be combined. For example, an illustrative embodiment may include features shown in connection with another illustrative embodiment.

FIG. 1 is a schematic depiction of a 4-step interface connection and sterilization process, in accordance with principles of the disclosure. In step 1/disconnected mode 101, two halves of chamber enclosure, namely first compartment-side 162 and second compartment-side 163 chamber enclosure components, are disconnected. Cavity 140 contains intracavitary cannular protrusion 165. Second compartment-side component 163 has surface protrusion 166. When first and second sides of interface are properly aligned, each intracavitary protrusion may be aligned with a surface protrusion (only one chamber and one of each type of protrusion is shown for simplicity).

In step 2/chamber connected mode 102, first compartment-side 162 and second compartment-side 163 chamber enclosure components are juxtaposed by action of linear actuator (not shown), which action is transmitted through connector 164, thereby forming chamber 144, containing intracavitary 165 and surface 166 protrusions, which remain axially aligned but detached.

In step 3/steam sterilization 103, steam is pumped into system via steam routing channels (see later figures), thereby sterilizing chamber.

In step 4/plug-socket connection 104, action of linear actuator induces intracavitary protrusion 165 to mate with surface protrusion 166, thereby establishing a fluidic connection between the conduits (not depicted) connected to each protrusion, while the first chamber 144 remains steam-tight.

Figure 2:
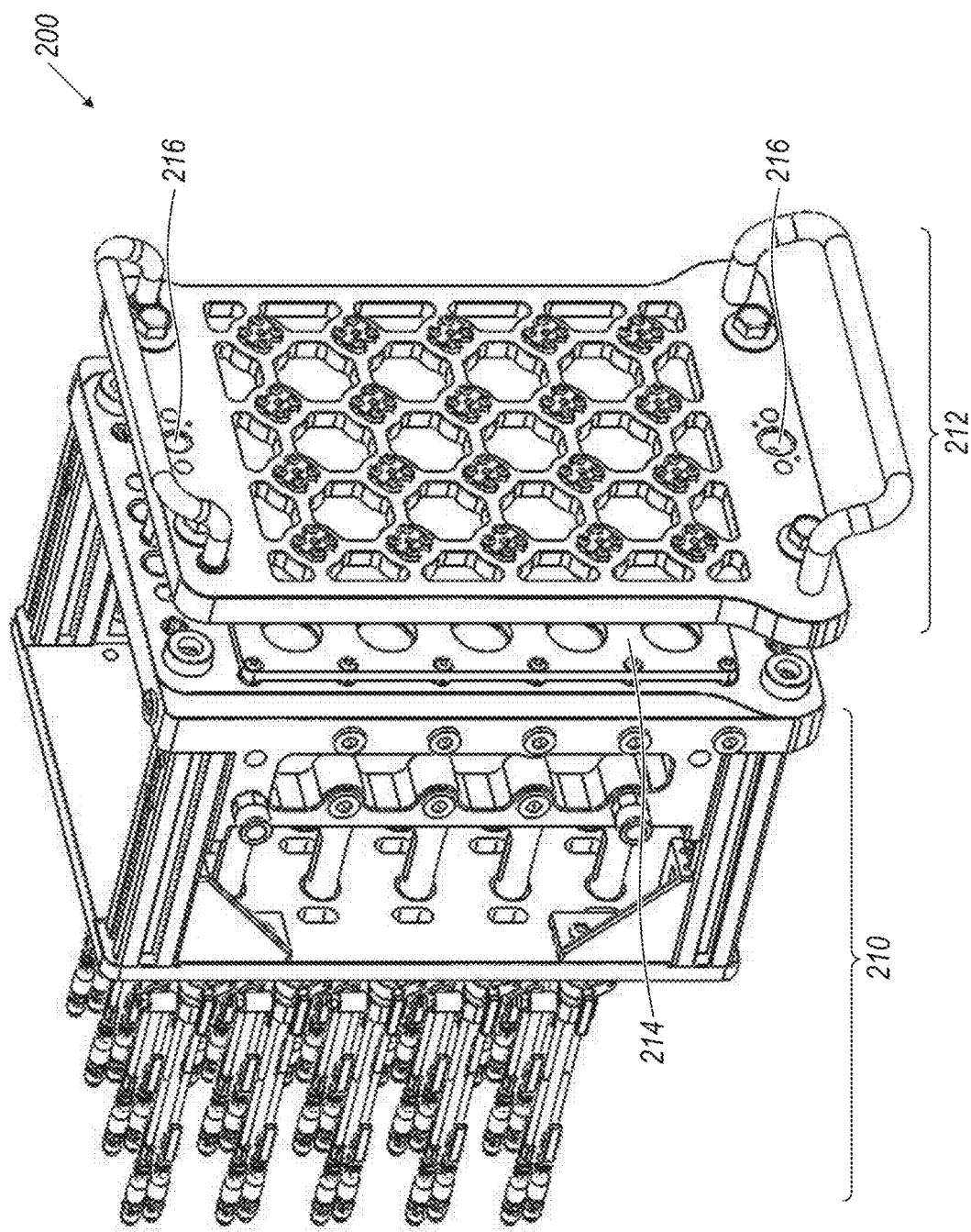
FIG. 2 depicts an oblique view of a reversibly connectable fluidic interface, in accordance with the principles of the described embodiments.

FIG. 2 depicts an oblique view of a reversibly connectable fluidic interface 200 (which may be also referred to as "slow interface"), including a first compartment side 210 and a second compartment side 212, in accordance with principles of the disclosure. First compartment side 210 of interface 200 has a substantially planar first face 214, which is mostly obscured in this view. First face 214 has an array of cavities, which is largely concealed in this view and shown in the next figure Alignment apertures 216 of second compartment side may receive first compartment-side rod-shaped protrusions (see FIG. 3). Alignment apertures 216 may be equal in number to the rod-shaped protrusions and in corresponding positions, and alignment apertures 216 may be positioned to enable alignment of the cavity array with the surface protrusion array (see other figures). Second compartment side 212 has a substantially planar second face (not visible in this view), which is configured to be pressed against the first face, thereby forming an array of steam-tight chambers, each of which is partially bounded by a cavity. The pressing may be actuated by a linear force. The force may be perpendicular to the plane of the array. The array of cavities on the first face has a mirror-image geometry relative to the array of surface protrusions on the second face.

Figure 3:
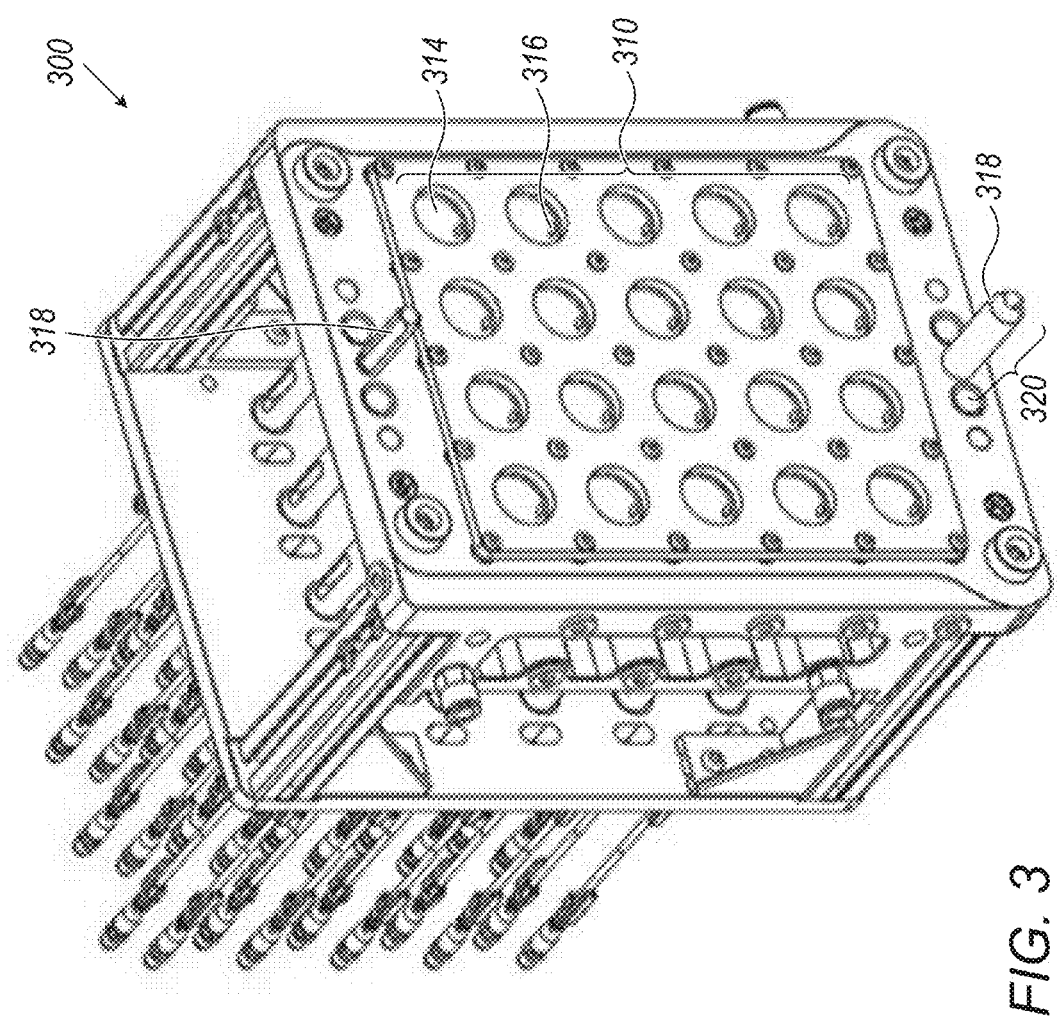
FIG. 3 depicts an isolated view of a side of a reversibly connectable fluidic interface, in accordance with the principles of the described embodiments.

FIG. 3 depicts an isolated view of first-compartment side 300 of a reversibly connectable fluidic interface (which may be also referred to as "slow interface"), showing an array 310 of twenty cavity openings, including first cavity opening 312 and a second cavity opening 314, in accordance with principles of the disclosure. Each cavity has a bottom draining steam outlet 316. Rod-shaped protrusions 318 are also visible. Each cavity has an intracavitary cannular protrusion, which are not depicted in this view. Rod-shaped protrusions may have a protruding dimension 320 that is greater than the dimension of the surface cannular protrusions (see FIG. 4).

Figure 4:
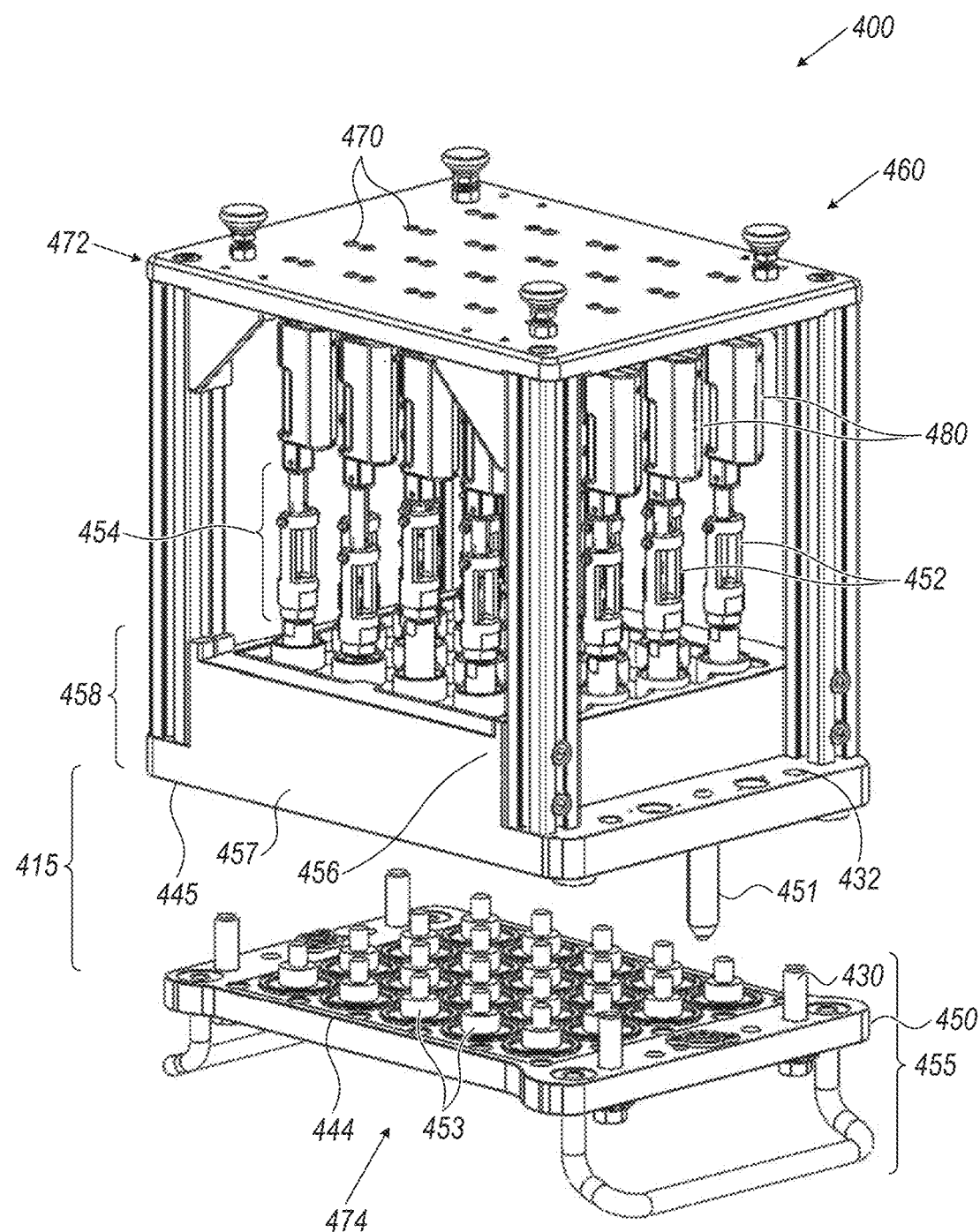
FIG. 4 depicts an isometric view of a steamable interface, including arrayed connectors, in accordance with the principles of the described embodiments.

FIG. 4 depicts an isometric, cutaway view of a fluidic interface (which may be also referred to as "slow interface"), including arrayed connectors, showing a possible array arrangement 454 of first compartment-side connectors 452 and linear actuators 480 of first compartment-side component 400 of interface 415, in accordance with principles of the disclosure. Attachment may be guided by 1-2 protrusions, one of which, 451, is visible in this view. Alignment pin 451 and first compartment-side connector termini (not visible) protrude from interface-side edge 445 of first compartment-side component 460. First compartment-side connectors 452 are slidably inserted in steam chamber block 458, for which proximal 456 and distal 457 sides are depicted. Surface cannular protrusions 453 are anchored in plate 450 and protrude from interface-side/proximal edge 444 (also referred to as "second face") of plate 450 of second compartment side 455. Bolts 430 are inserted into bolt apertures 432 and may serve to anchor plate 450 against steam chamber block 458.

The interfaces shown in this and the other figures may be usable in both the upstream and downstream apparatuses (depicted in later figures), although the sterilization step may be optional for the downstream apparatus. First and second conduits on the first compartment side may run from first and second connectors 452 through small apertures 470 in distal wall 472 of first compartment-side component 4 (see FIG. 18). First compartment-side conduits may fluidly connect to each intracavitary protrusion. Third and fourth conduits on the second compartment side (not shown) may protrude from distal side 474 of plate 450 and fluidically connect to surface protrusions 1753. Second compartment-side conduits may fluidly connect to each surface protrusion.

Figure 5:
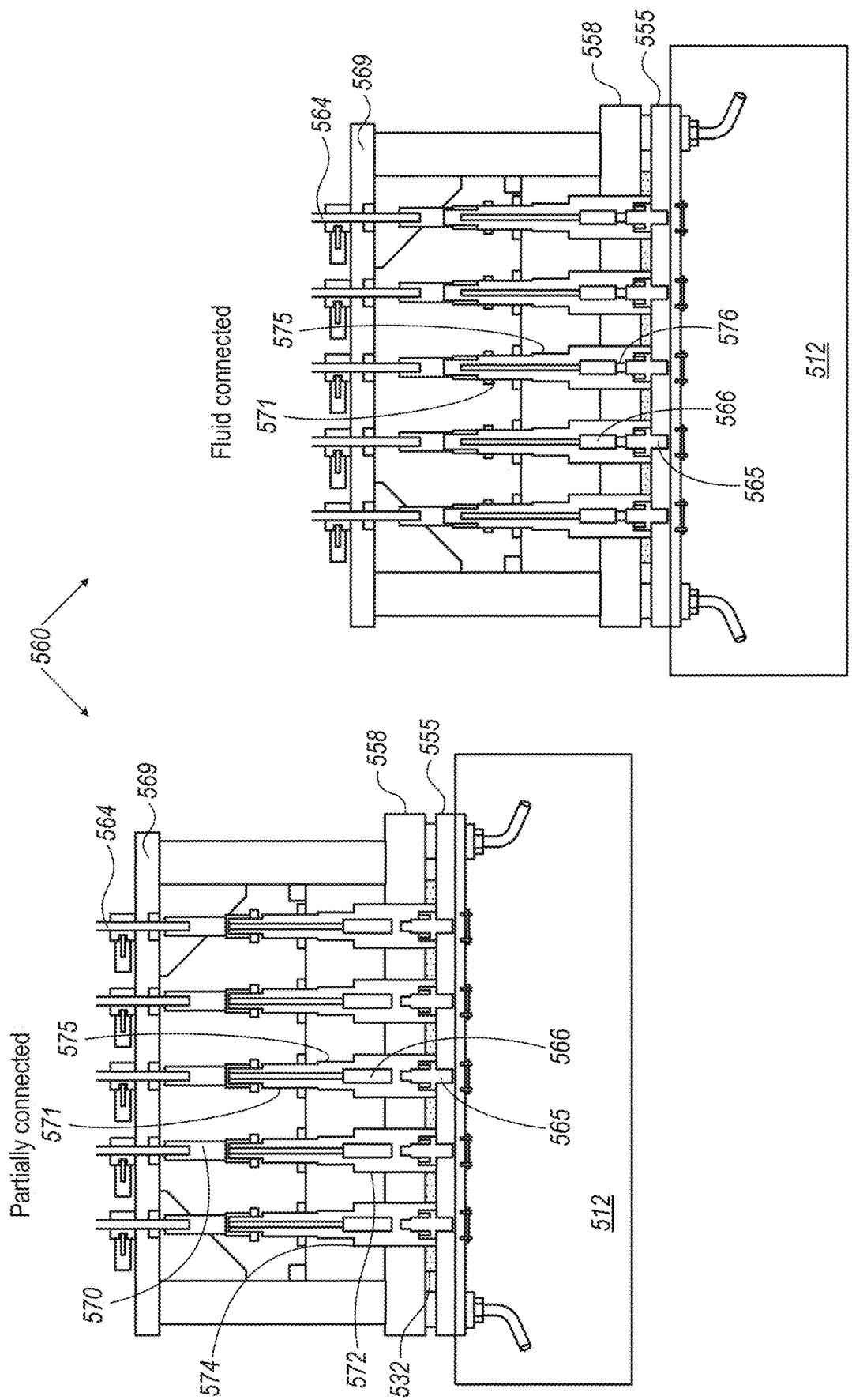
FIG. 5 depicts a side view of a first-side component of a described interface and its connection to a second compartment, in accordance with the principles of the described embodiments.

FIG. 5 depicts a side view of the first compartment-side interface component 560 and its connection to a second compartment (or "slow module"), depicted schematically as box 512, in accordance with principles of the disclosure. Within first compartment-side component 560, chamber linear actuator 564 traverses optional distal wall 569 via apertures (not depicted) and rigidly connects to retaining piece 570, which itself rigidly connects to connector 571. Directions of motion of chamber linear actuator 564 and fluid/air flow path are parallel to axis of chamber linear actuator 564. Prior to chamber-connected mode, plate 555 of second compartment may have been pre-sterilized separately, e.g., in an autoclave.

Chamber-connected mode (left panel; parallels step 2 of FIG. 1) is attained by moving plate 555 into contact with gasket seal 532 using a plate actuator (not shown), forming airtight steam chamber 572, which chamber is bounded by connector 571, block 558, and plate 555. Steam chamber 574 may include piston seal 575. Surface protrusions 565 and intracavitary protrusions 566 remain detached from one another.

In the next step (not depicted; parallels step 3 of FIG. 1), steam chamber 574 is steam-sterilized through chambers formed by plate 555 and (first compartment-side) steam chamber block 558. Steam is routed through block 558 via several inlets (not depicted).

In fluid-connected mode (right panel; parallels step 4 of FIG. 1), actuator fully engages downward to move intracavitary protrusions 566 downward, thus mating with surface protrusions 565 to form fluid connections 576. Fluid connections 576 may be simultaneously or independently actuated. Second compartment may be totally passive. Second compartment may lack actuators and sensors.

FIG. 6 depicts a cutaway view of a steam chamber block 458, in accordance with principles of the disclosure. First 620 and second 622 cavities are cut away from the end proximal to the first compartment (an orientation essentially opposite to FIG. 3). Steam inlet openings 624 are gaseously connected to the array 630 of cross-drilled steam distribution channels 626 are also depicted.

FIG. 7 depicts a cross-sectional, side view of steam chamber block 458, in accordance with principles of the disclosure. Depicted are first 720 and second 722 cross-drilled steam inlets and arrows 724 showing steam inlet flow. Dotted arrow 726 shows possible preferential steam feeding to a chamber 728 with a lower steam pressure than other chambers 730.

FIG. 8 depicts another cross-sectional, side view of steam chamber block 458, in accordance with principles of the disclosure. First 820 and second 822 cross-drilled steam outlets and steam outlet flow arrows 824 are shown.

Figure 9:
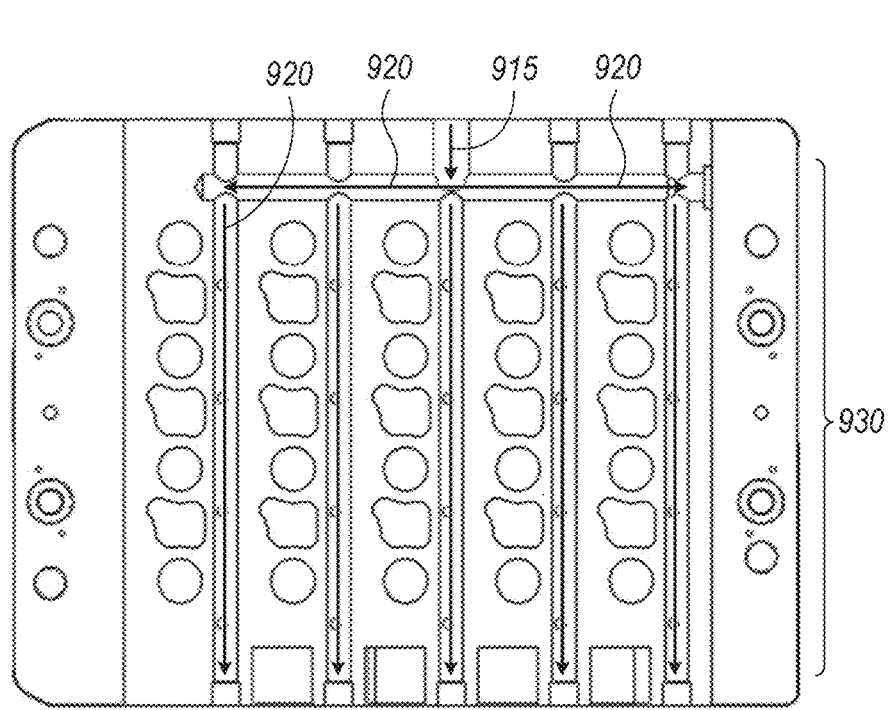
FIG. 9 depicts a cross-sectional, top view of a steam chamber block, in accordance with the principles of the described embodiments.

FIG. 9 depicts a cross-sectional, top view of steam chamber block 458, in accordance with principles of the disclosure, showing common steam entry point 915 and parallel main distribution lines (arrows 920) of array 930 of steam distribution channels.

Figure 10A:
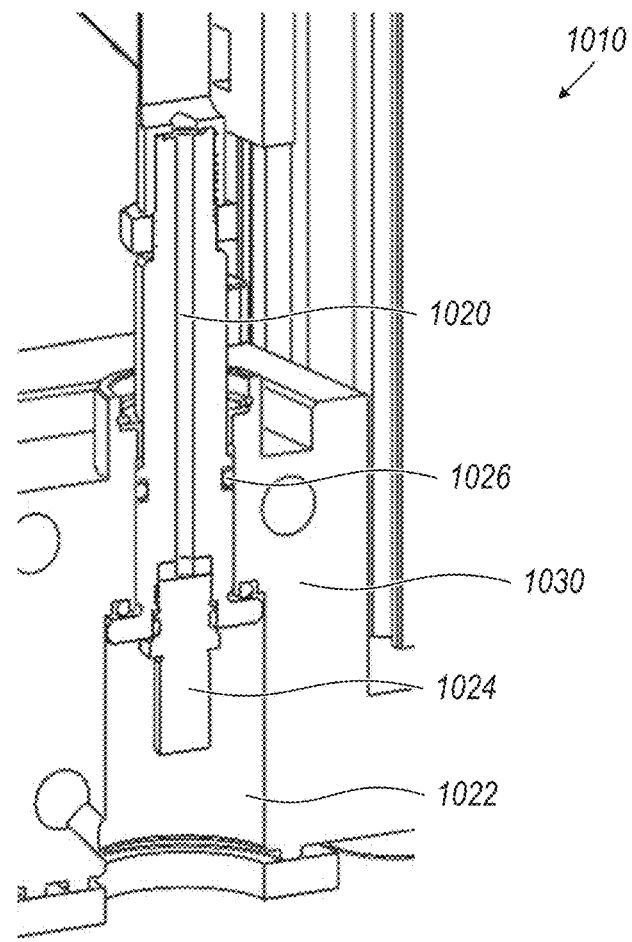
FIGS. 10A-B depict cross-sectional, side views of a single actuator-chamber assembly in plug-socket disconnected (A) and connected (B) view, in accordance with the principles of the described embodiments.

FIG. 10A depicts a cross-sectional, side view of a single actuator-chamber assembly 1010 in chamber-sealed position, in accordance with principles of the disclosure. Connector 1020, chamber 1022, and intracavitary cannular protrusion 1024 are depicted. O-ring-shaped piston seal 1026 may provide a steam-tight seal between connector 1020 and steam chamber block 1030.

Figure 10B:
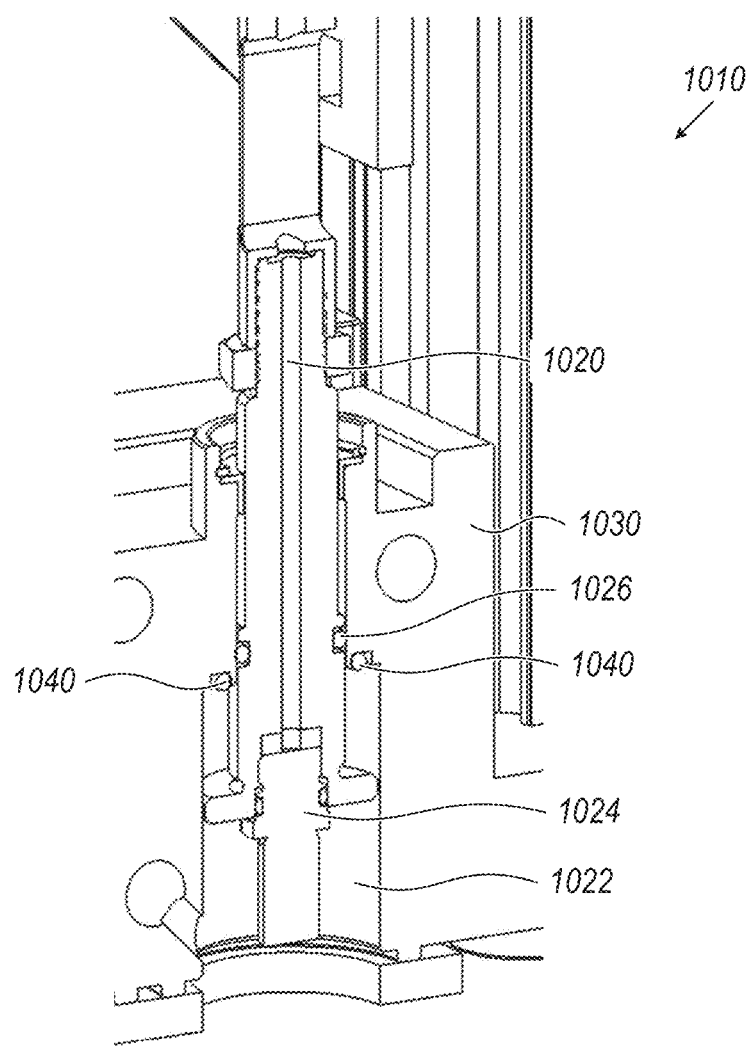

FIG. 10B depicts a cross-sectional, side view of an actuator-chamber assembly 1010 after consummating the plug-socket connection, in accordance with principles of the disclosure. Connector 1020, O-ring-shaped piston seal 1026, and intracavitary protrusion 1024 have moved downward towards the interior of chamber 1022. O-ring-shaped piston seal 1026 may be located slightly above the ceiling 1035 of chamber 1022. Face seal O-ring 1040 may cushion connector 1020 and steam chamber block 1030 from collision when connector 1020 subsequent retracts.

Figure 11:
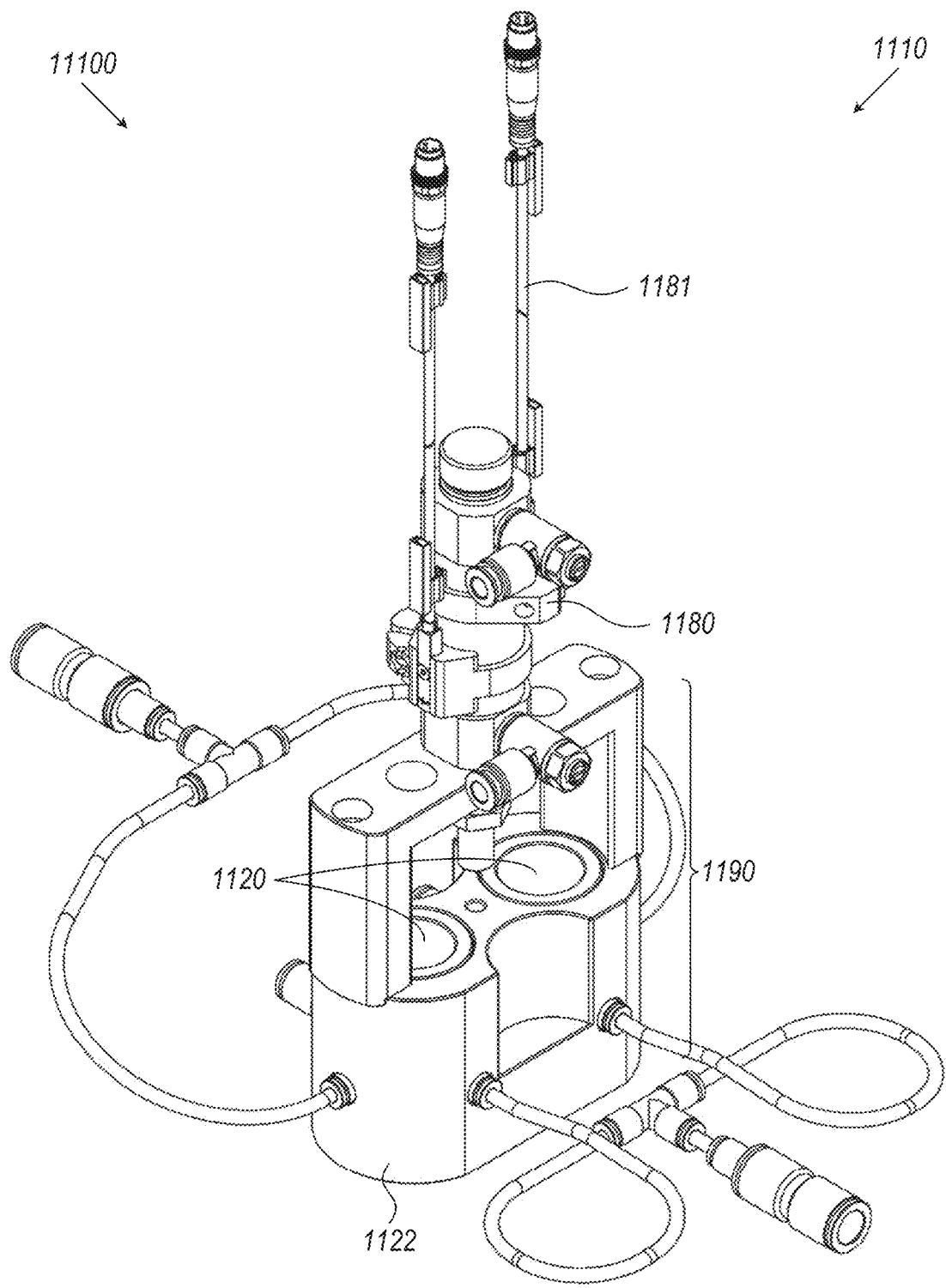
FIG. 11 depicts an isometric view of a connecting apparatus, including a first-side interface component and components disposed proximally thereto, in accordance with the principles of the described embodiments.

FIG. 11 depicts an isometric view of first compartment-side components 1110 of a fluid interface between a first and second conduit (not depicted), such that axial dimension of cavities 1120 stands upright, in accordance with principles of the disclosure. Depicted components include rigid framework 1190, hosting cavities (which form first compartment-side components of steam chambers) 1120 and components disposed proximally (internally) thereto, including actuators 1180 and actuator sensor cables 1181. The described fluid interface may also be referred to herein as a "fast module" interface. The first compartment-side components 1110 may be housed in a first compartment (not depicted). There may be a second compartment (not depicted). The second compartment-side components of the interface may have 1-2 surface cannular protrusions (not shown) protruding therefrom and may be similar to the second compartment-side components depicted in FIG. 4, except that the number of protrusions is smaller and may be commensurate with the number of cavities 1120 in the first compartment. One or more surface protrusions from the second compartment may be fluidly connected to a conduit disposed in the second compartment.

With further reference to FIG. 11, block 1122 houses cavities 1120. Surface perforations of cavities 1120 are on the underside of block 1122 and thus not visible in this view. Rather, cavities 1120 are visible because block 1122 is sectioned horizontally.

Figure 12:
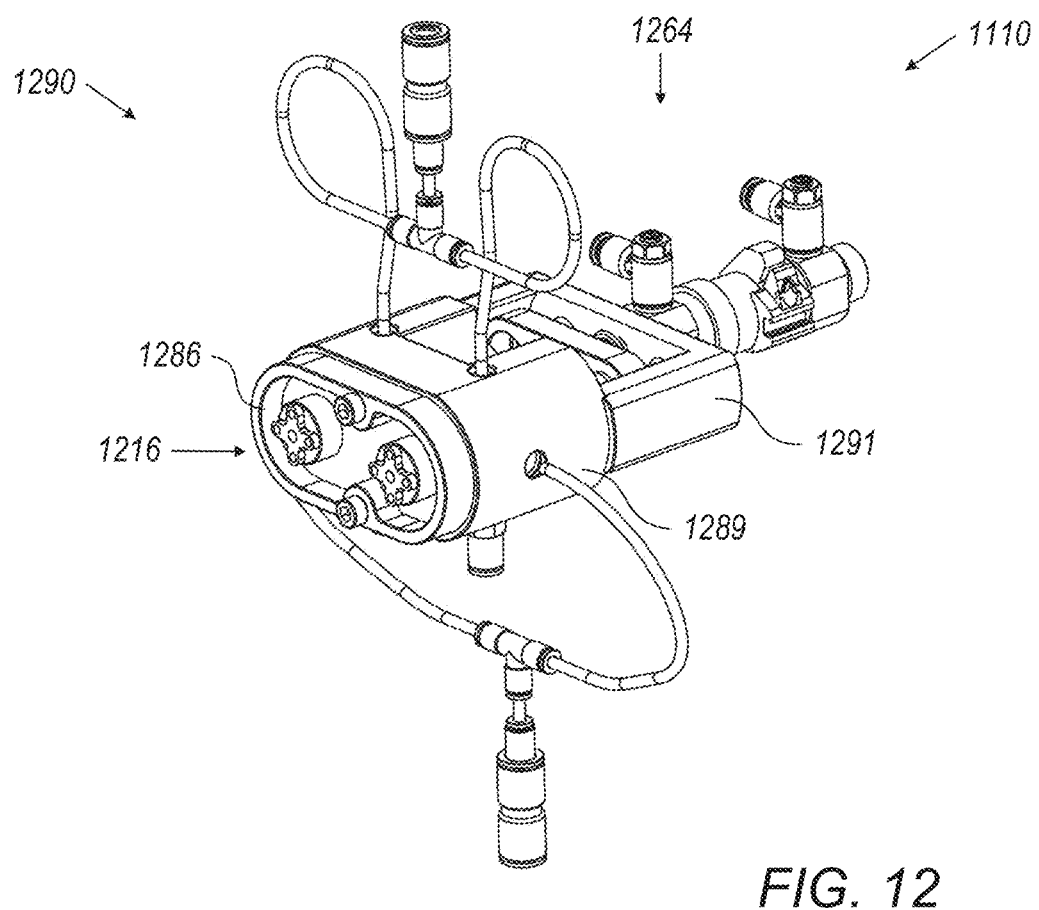
FIG. 12 depicts an oblique view of a connecting apparatus, including a first-side component of an interface and components disposed proximally thereto, in accordance with the principles of the described embodiments.

FIG. 12 depicts an oblique, isolated view of the components 1110 of a fluid interface 1216 (also referred to as "fast module interface"), in accordance with principles of the disclosure. View angle is rotated approximately 90° in both the frontal and horizontal planes relative to FIG. 11, such that chambers lie horizontally, side by side. Depicted are second-compartment plate (also referred to as "substantially planar second face") 1286, chamber housing block 1289, actuator mount 1291, and linear actuator 1264. The mechanism of attachment of fast module and its individual connectors may be similar to that of slow module (FIGS. 2-10).

Figure 13:
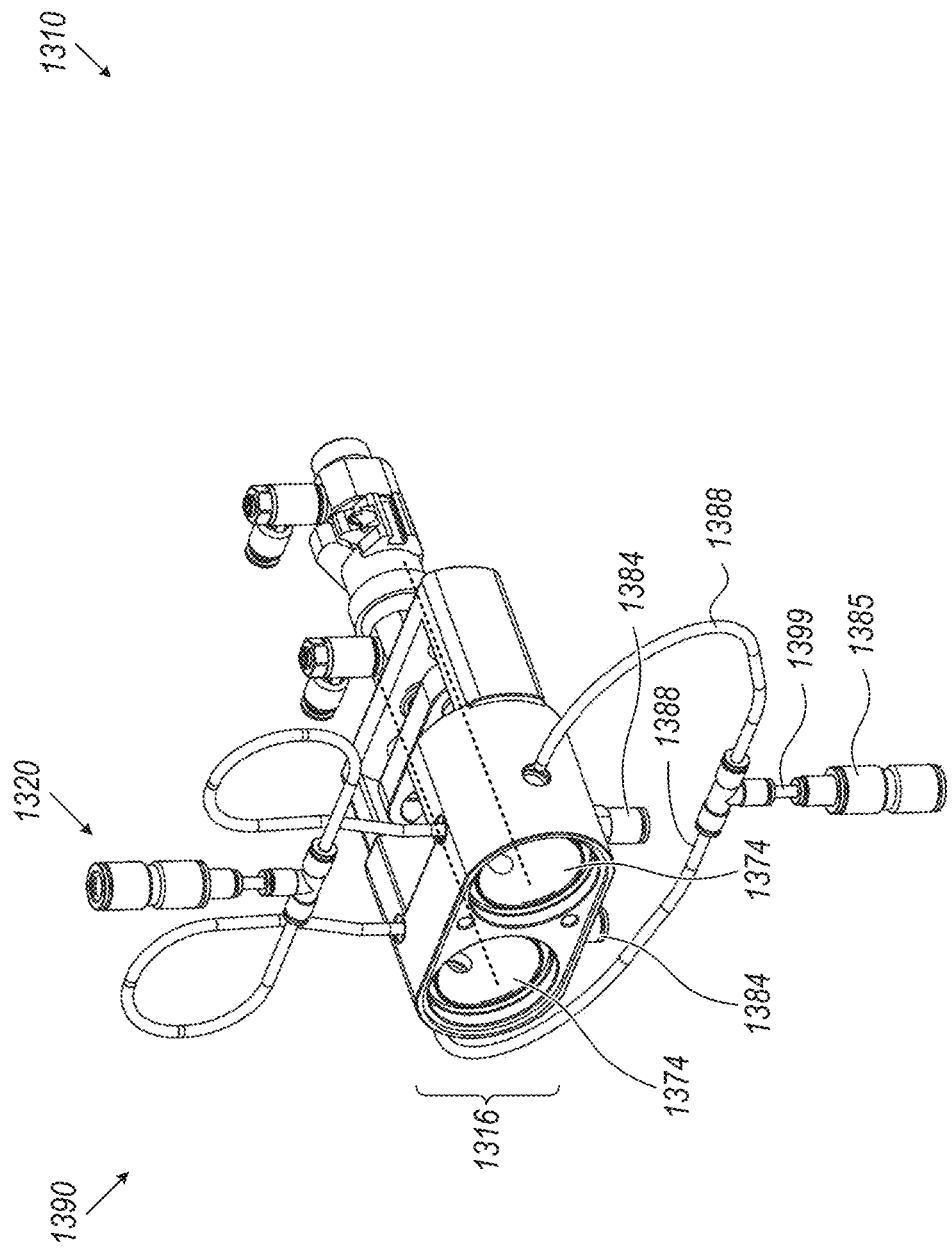
FIG. 13 depicts an oblique view of a first-side component of an interface, in accordance with the principles of the described embodiments.

FIG. 13 depicts an oblique, isolated view of the first compartment-side components 1310 of a fluid interface, in accordance with principles of the disclosure. View angle is the same as the previous Figure. The view with the fast module fast module second compartment removed enables visualization of cavities 1374, which may be used to form two steam-tight chambers (also referred to as "steam chambers") after pressing against a second compartment (not depicted).

Cooling inlet/outlet tubes 1384 enable circulation of water from a pump (not depicted) through cooling channels (see description of next figure).

Steam for sterilization first passes through steam inlet connector 1385 and inlet line 1399, which splits into two peripheral inlet lines 1388, one for each cavity 1374. Steam exits via chamber steam outlet 1320.

Fluid flow through the interface 1316 is depicted by dotted lines. Fluid paths within central side component 1390 are not visible in this view.

Figure 14:
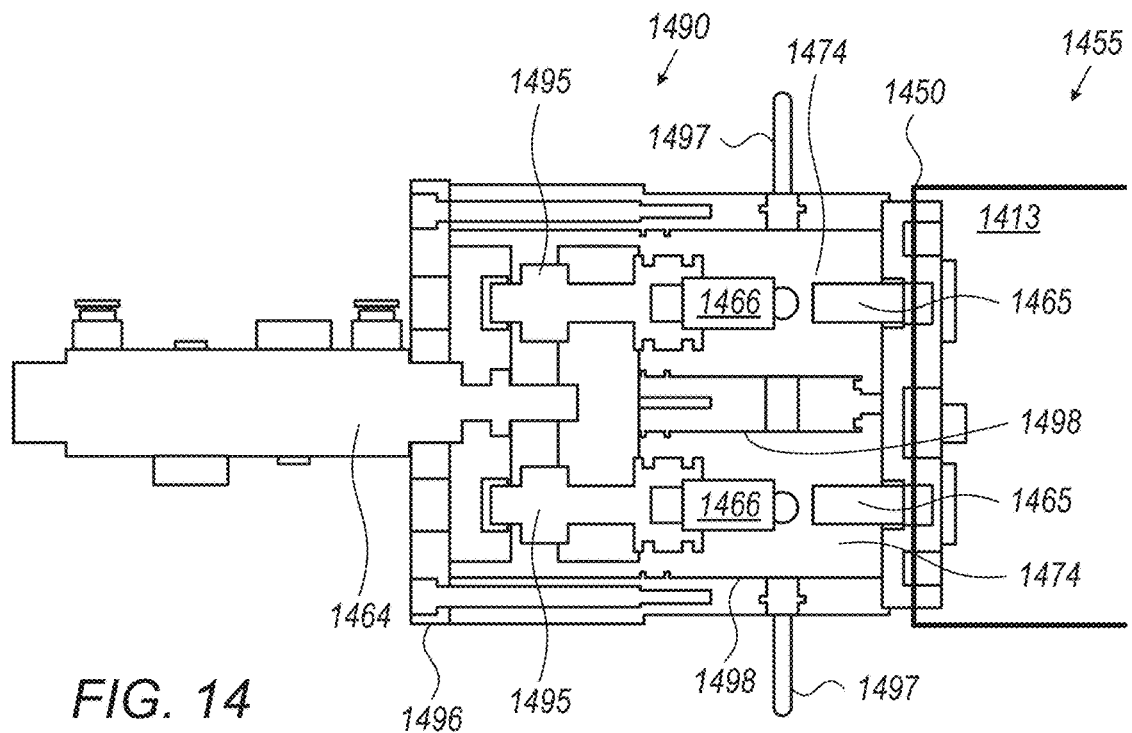
FIG. 14 depicts a top, cross-sectional view of components of an interface, in accordance with the principles of the described embodiments.

FIG. 14 depicts a top, cross-sectional view (relative to FIGS. 12-13), sectioned longitudinally through the steam-tight chambers 1474, of first compartment-side components 1490 of interface 1455 (also referred to as "fast module interface") and second compartment 1413 (depicted schematically as a box), in accordance with principles of the disclosure.

With further reference to FIG. 14, intracavitary cannular protrusions 1466 and surface cannular protrusions 1465 are located within chambers 1474. Intracavitary protrusions 1466 may be fluidly connected to first compartment-side conduits (not depicted). Interface 1490 is depicted in chamber-connected, but fluid-disconnected, position/mode, in which surface protrusions 1465 and intracavitary protrusions 1466 are located within chambers and are axially aligned but separated. Chambers 1474 were created from cavities (see FIG. 13) by pressing flat surface 1450 of second compartment 1413 against first compartment 1490, sealing openings of cavities and thus forming chambers 1474. Pressing second compartment 1413 against first compartment 1490 also inserts surface protrusions 1465 into lumen of chambers 1474. Surface protrusions 1465 may be fluidly connected to second compartment-side conduits (not depicted). Proximal ends 1495 of fluid connectors are depicted. Proximal end 1496 of first compartment-side component 1490 may be rigidly connected to remainder of first compartment, for example by attachment to a plate (not depicted) mounted on a rigid frame. Two-headed arrow denotes direction of motion of linear actuator 1464. Tubing 1497 is described as steam inlet lines in the previous figure. Subsequent force provided by linear actuator 1464 moves connectors and intracavitary protrusions 1466 rightward, causing each to mate with and form a fluid-tight luminal connection with surface protrusions 1465, as depicted in FIGS. 1 and 5. Cooling channels (not depicted) approximately one millimeter wide surround outer edges 1498 of chambers 1474, enabling rapid cooling after steam sterilization.

Figure 15:
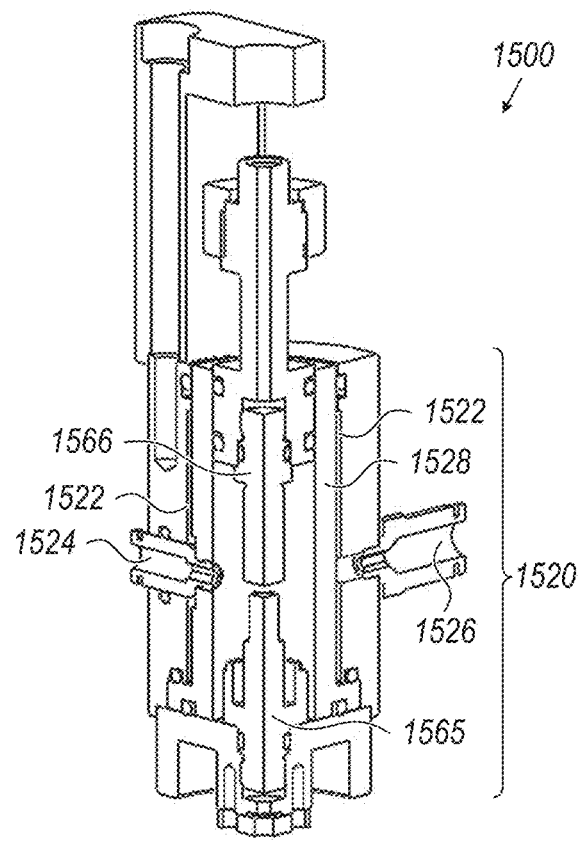
FIG. 15 depicts a cross-sectional view of components of an interface, in accordance with the principles of the described embodiments.

FIG. 15 depicts a two-plane cross-sectional view of components 1500 of an interface (also referred to as "fast module interface"), sectioned longitudinally through a single chamber 1520, in accordance with principles of the disclosure. Cooling channel/water jacket 1522, intracavitary protrusion 1566, steam inlet 1524, and cooling water inlet 1526 are depicted. Waterproof boundary 1528 divides chamber 1520 from cooling channel 1522. Surface protrusion 1565 has been inserted into cooling channel 1520, but not yet brought into contact with intracavitary protrusion 1566.

Figure 16:
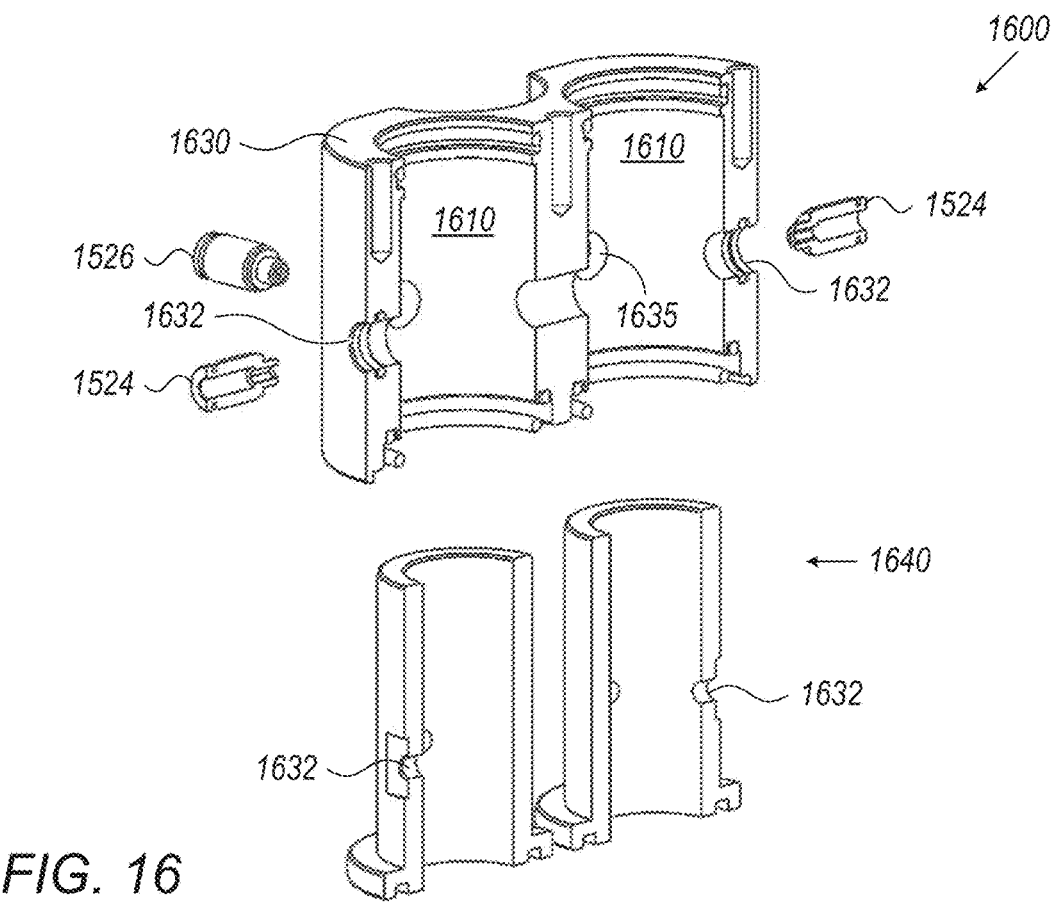
FIG. 16 depicts an exploded, cross-sectional view of 2 chambers, in accordance with the principles of the described embodiments.

FIG. 16 depicts an exploded, cross-sectional view 1600 of 2 chambers 1610, showing insertion of cooling water inlets through cooling channel, in accordance with principles of the disclosure. Inserts 1640 are configured to slide into outer framework 1630, thus forming chamber 1610. Insertion of inserts 1640 into outer framework 1630 also forms a single cooling channel between (not visible in this view) inserts 1640 and outer framework 1630. Cooling chamber surrounds both chambers 1610, whose cooling channel areas are liquidly connected by aperture 1635. After insertion of inserts 1640 into outer framework 1630, steam inlet 1524, and cooling water inlet 1526 are bolted into side apertures 1632 and rear apertures (not visible).

Figure 17:
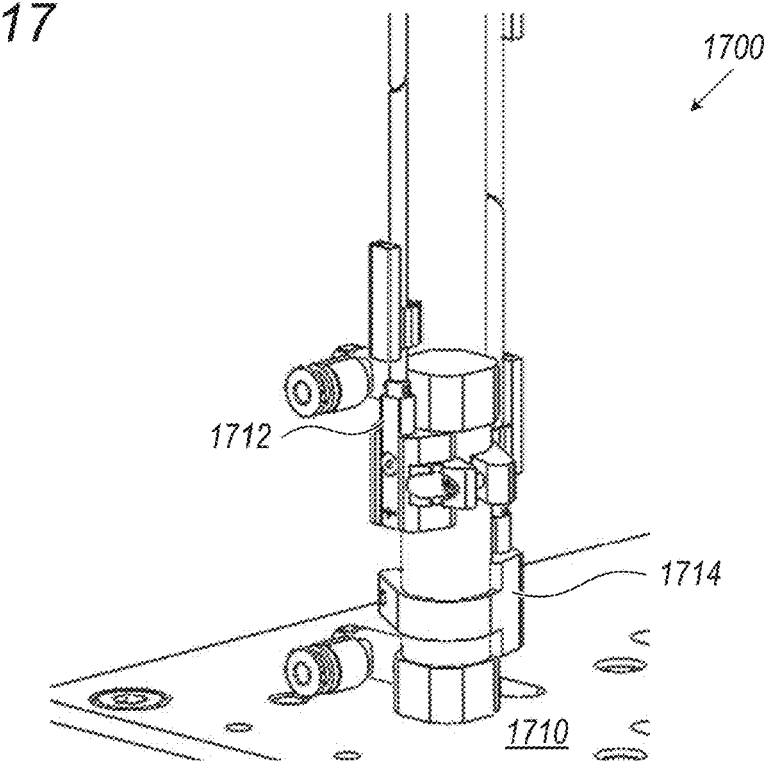
FIG. 17 depicts an isolated view of a single actuator, in accordance with the principles of the described embodiments.

FIG. 17 depicts an isolated view of a single actuator 1700, in accordance with principles of the disclosure. Actuator 1700 is embedded in an optional distal wall 1710, which may function similarly to distal wall 569 of FIG. 5. Two optional limit switches 1712, 1714 or sensors are shown in disconnected 1712 and connected 1714 position. One or more of switches 1712 and 1714 may be used to detect proper connection and disconnection between intracavitary protrusions and surface protrusions (not visible in this view).

Figure 18:
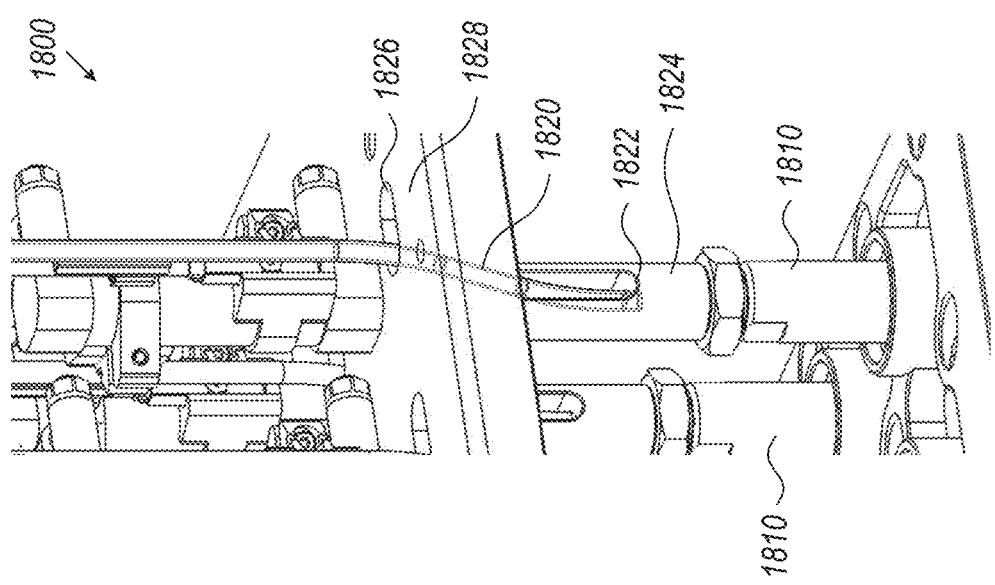
FIG. 18 depicts an isolated view of two connectors of a component of an interface, in accordance with the principles of the described embodiments.

FIG. 18 depicts an isolated view 1800 of two connectors 1810 of a first compartment-side component of an interface (also referred to as "slow module interface"), in accordance with principles of the disclosure. View shows path of a representative tube or conduit 1820 from flanged conduit end (see FIGS. 19-20) through side aperture 1822 in retaining piece 1824 and top aperture 1826 in distal wall 1828.

Figure 19:
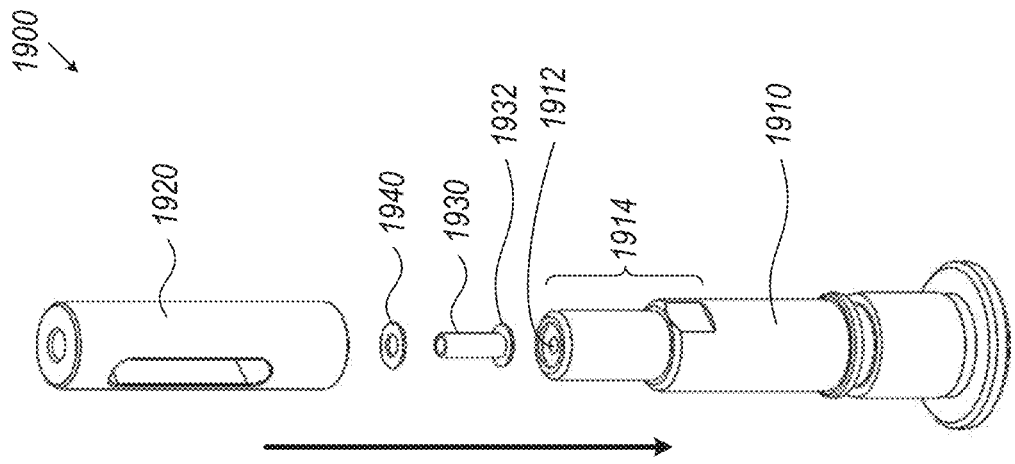
FIG. 19 is an exploded view of a piston flanged conduit assembly, in accordance with the principles of the described embodiments.

FIG. 19 is an exploded view of a flanged tube or conduit 1900. Direction of assembly is shown by arrow. Oblong connector 1910 is substantially cylindrical and has a substantially circular cross section. Connector 1910 contains a depression 1912 that may be substantially circular on its end surface. Flange 1932 of conduit end 1930 and rigid, perforated disk (which may be referred to as a "washer") 1940 fit inside depression 1912. Retaining piece 1920 is substantially cylindrical and has a substantially circular cross section. Retaining piece 1920 contains lower aperture (not visible) that fits over conduit tube end 1930, disk 1940, and tapered distal end 1914 of connector 1910. Attachment of retaining piece 1920 to connector 1910, over distal end 1914, may serve to exert axial pressure and press disk 1940 deeper into depression 1912, compressing flanged conduit end 1930. Flange 1932 may form a steam-tight seal against connector 1910 and may constitute the ceiling of a steam-tight chamber inside connector 1910. Conduit end 1930 may be the end of a conduit extending upward, for example as depicted in FIG. 18.

Figure 20:
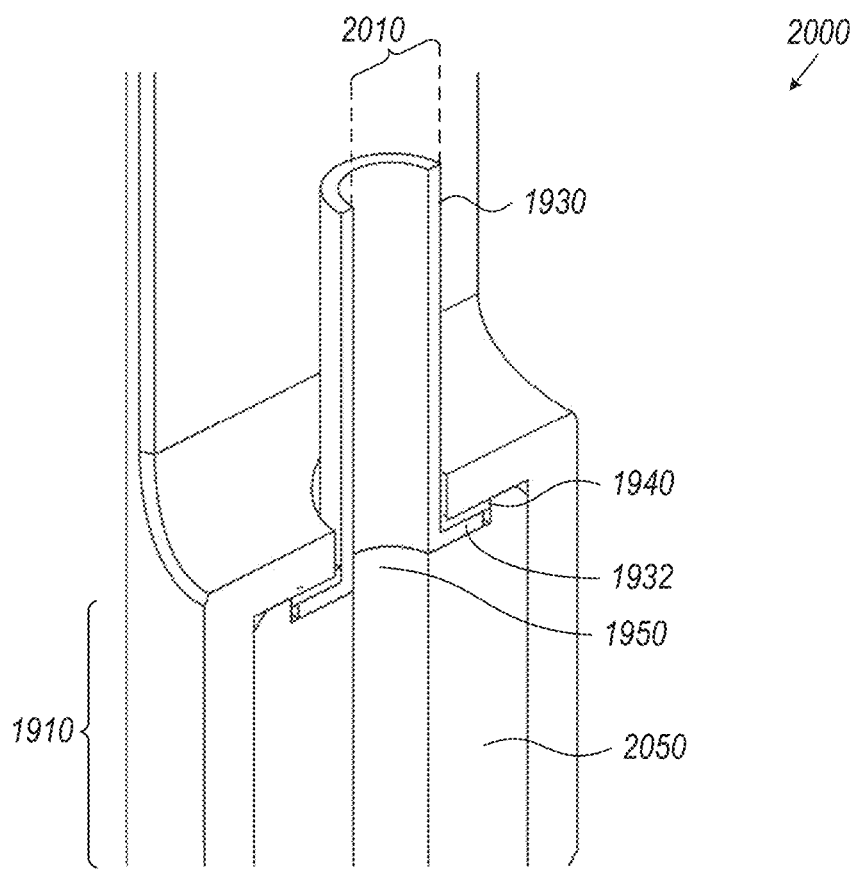
FIG. 20 is a magnified cross section of a flanged conduit assembly, in accordance with the principles of the described embodiments.

FIG. 20 is a magnified cross section of an assembled flanged conduit 2000, showing continual internal bore 2010, as well as assembly of retaining piece 1920, disk 1940, conduit end 1930 with flange 1932, and connector 2050. Upper surface of connector is located immediately below flange 1932. Cross-sectional view reveals chamber 2050. Internal bore 2010 may align with a bore 1950, which traverses connector 2050. Connector 1910 is hidden from view.

Figure 21:
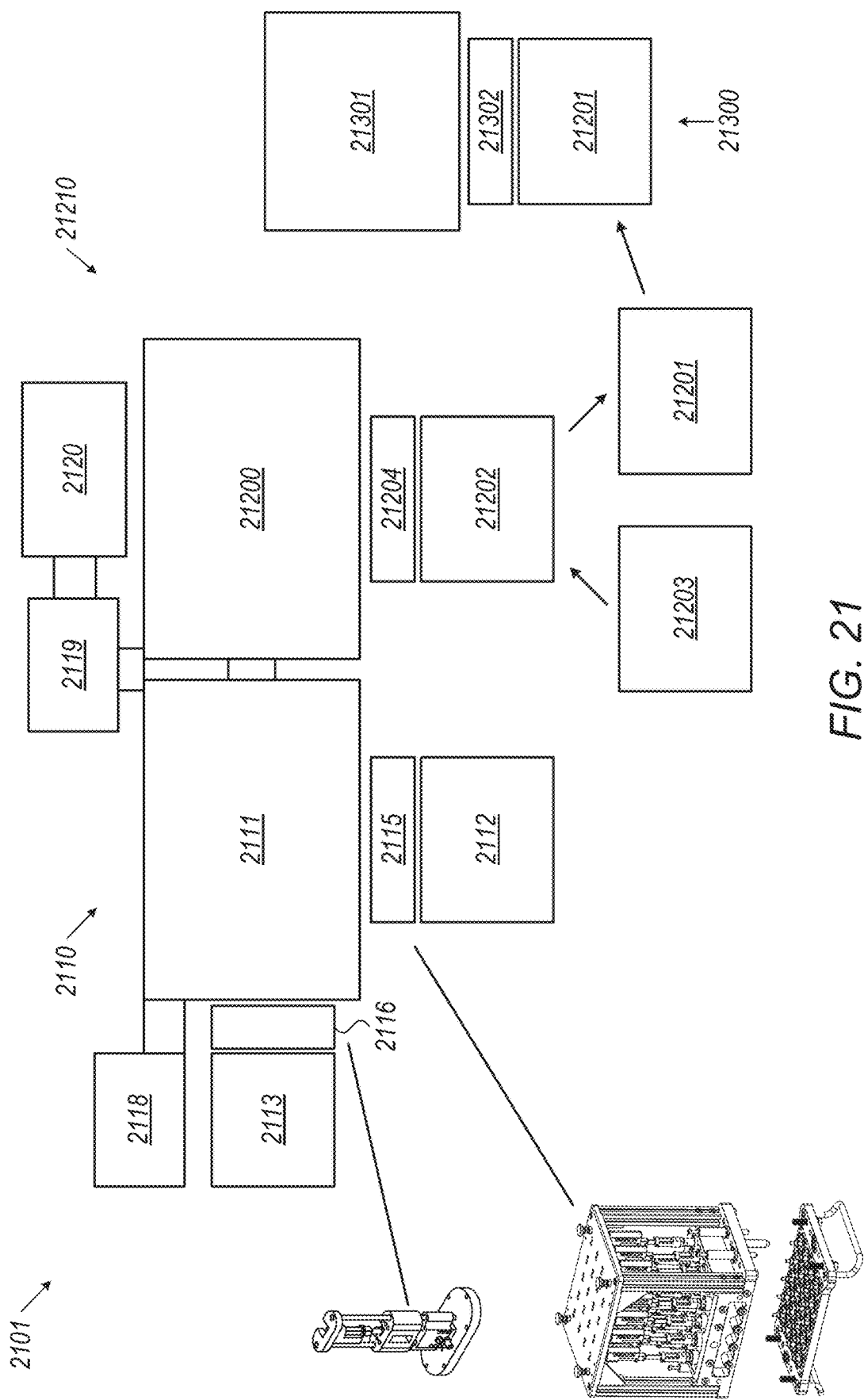
FIG. 21 is a schematic system architecture overview, in accordance with the principles of the described embodiments.

FIG. 21 is a schematic system architecture overview of system 2101, in accordance with principles of the disclosure. System 2101 includes upstream apparatus 2110 and downstream apparatus 21210. Upstream apparatus includes first compartment 2111, which may be fixed in place and contains bioreactor chamber (not depicted). First compartment connects to "slow" upstream module 2112 (or "second compartment") and "fast" upstream module 2113 (or "additional second compartment"), containing fluid containers (not depicted), via slow 2115 and fast 2116 module interfaces, respectively. First compartment 2111 also may connect to utility lines 2118 (depicted schematically by box), such as gas, steam, and cleaning fluid. Upstream apparatus 2110 and/or downstream apparatus 21210 may be connected to power/data lines 2119, which in turn may connect to supervisory control and data acquisition system 2120.

With further reference to FIG. 21, first compartment 21200 of downstream apparatus 21210 may connect sequentially to second compartments 21201-21203 via downstream interface 21204, which may be identical in structure to slow module interface 2115. Module handling system 21300, including Reuse (Clean/Sterilize/Fill) Station 21301, can be used to clean any of downstream second compartments 21201-21203 (depicted for downstream second compartment 21201) via cleaning interface 21302.

Figure 22:
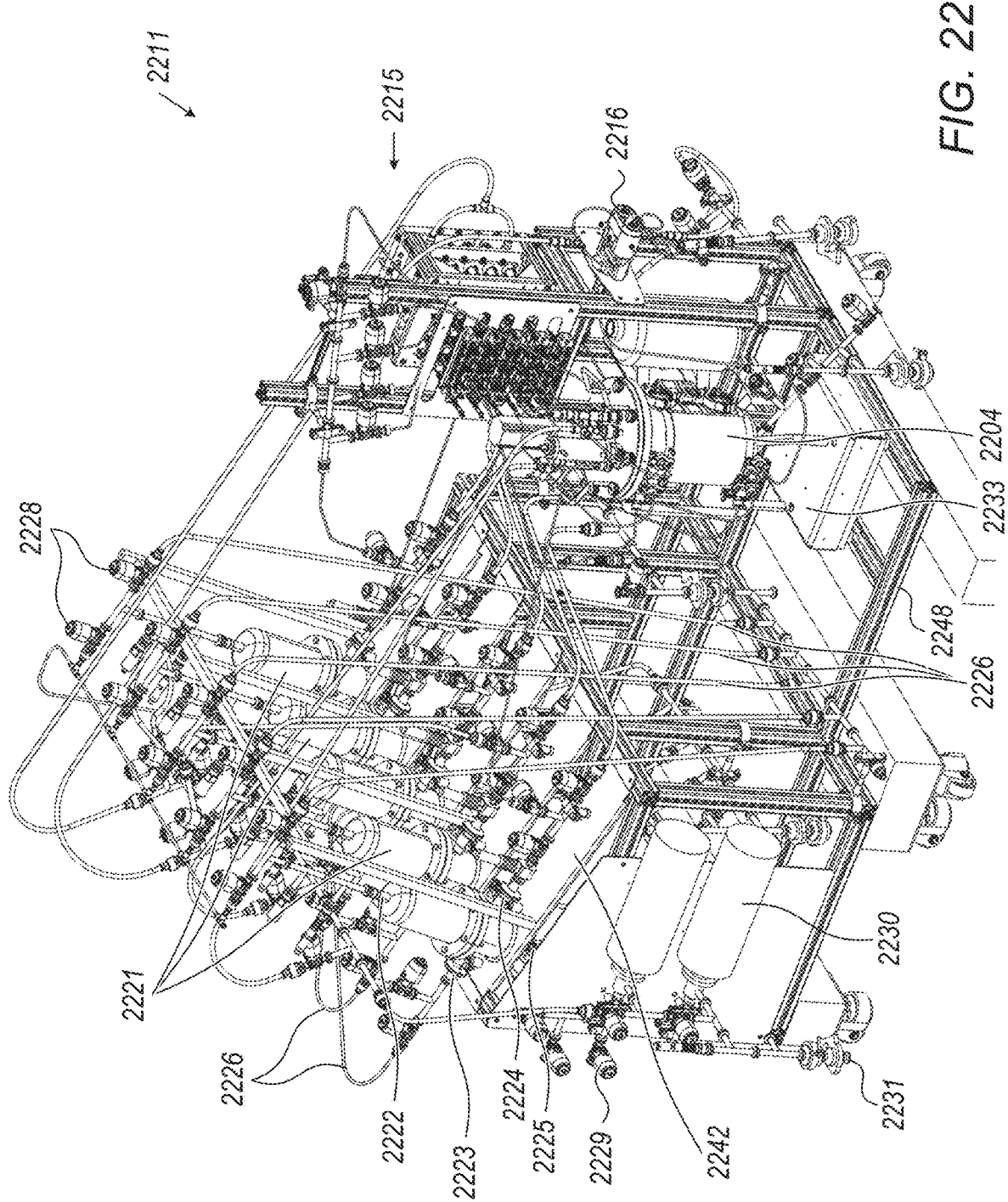
FIG. 22 shows an oblique view of a first compartment of a system, in accordance with the principles of the described embodiments.

FIG. 22 shows an oblique, cutaway view of first compartment 2211 of upstream apparatus, in accordance with principles of the disclosure. Sterile air filters 2221 are connected via air lines 2226, which can carry air to an upstream pressure regulator. This regulator sets and maintains the inlet air pressure to induce air flow through the filter. Temperature and pressure are measured using sensors. Each sterile air filter 2221 has a vent 2222 an inlet 2223, an outlet 2224, and a drain 2225. Valves 2228 are placed at each of these ports to control flow through different paths through or around the filter. The flow path depends on whether an automated sterilization protocol or process protocol is being run. Bioreactor 2204 and attachment sites of slow 2215 and fast 2216 modules (see below) are also depicted. Sterile air filters 2221 and associated apparatus are attached to and supported by rigid baseplate 2242. Depicted components are attached to, held in place, and supported by rigid frame 2248.

Steam enters filters 2221 through their inlet 2223, traverses the filter membrane (not depicted), and exits via the outlet 2224. The vent 2222 and drain 2225 may be used for pre-heating air filters 2221 and filter integrity testing. The auxiliary utility valves 2229 (which can be used for water, cleaning fluid, and steam) and equipment are used to route steam into the system from optional control valves 2230, and route condensate out of the system through a system of system drains 2231. Pipes may be angled for optimal draining.

The bioreactor 2204 may rest on a scale 2233 to continuously or periodically monitor the mass inside the bioreactor. As fluid is added or samples are removed from the bioreactor, its mass will change, from which the flow rate and mass transfer can be deduced.

A "Slow" module (or "second compartment") may connect to first compartment 2211 at a first attachment site 2215. A "Fast Addition" or "additional second" module may attach at a second attachment site 2216. These module(s) can also be used to take samples. The Fast Addition module may be steam-sterilized and actively water cooled to speed up the connection/disconnection process. Similar components may be present in first compartment of downstream apparatus.

Figure 23:
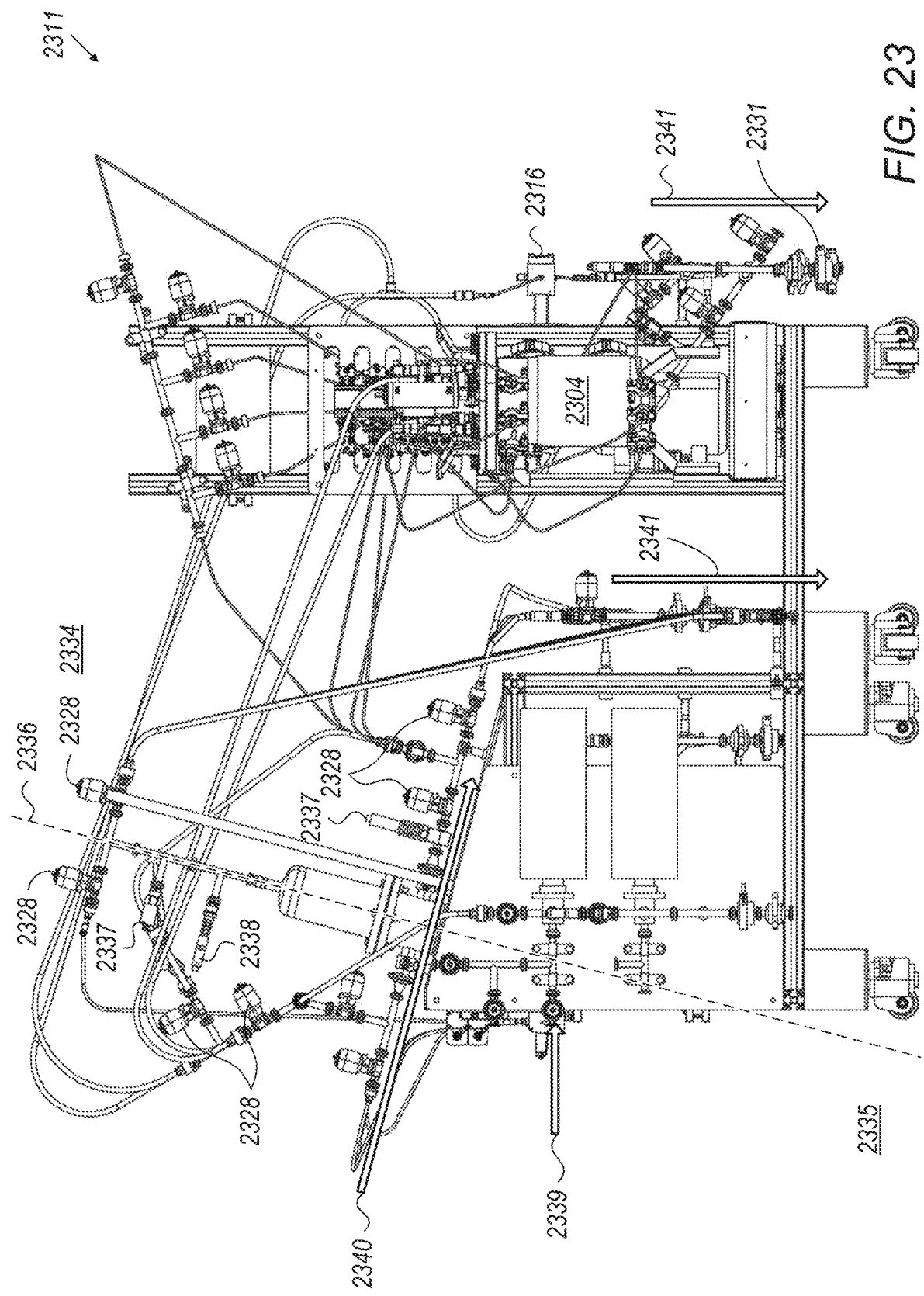
FIG. 23 depicts a side view of a first compartment of a system, in accordance with the principles of the described embodiments.

FIG. 23 depicts a side view of first compartment 2311 of upstream compartment or apparatus, highlighting the separation between sterile air side 2334 and non-sterile air side 2335, created by sterile filter membrane (demarcated by dotted line 2336), in accordance with principles of the disclosure. The sterile filter may prevent microbes to pass through its membrane, maintaining sterility on the sterile air side. The sterile boundary is also maintained across the two interfaces. Fast addition interface 2316, valves 2328, system drains 2331, pressure 2337 and temperature gauges 2338, and main steam inlet 2339 are also depicted. Diagonal arrow 2340 shows air flow direction. Vertical arrows 2341 show condensation flow direction.

Figure 24:
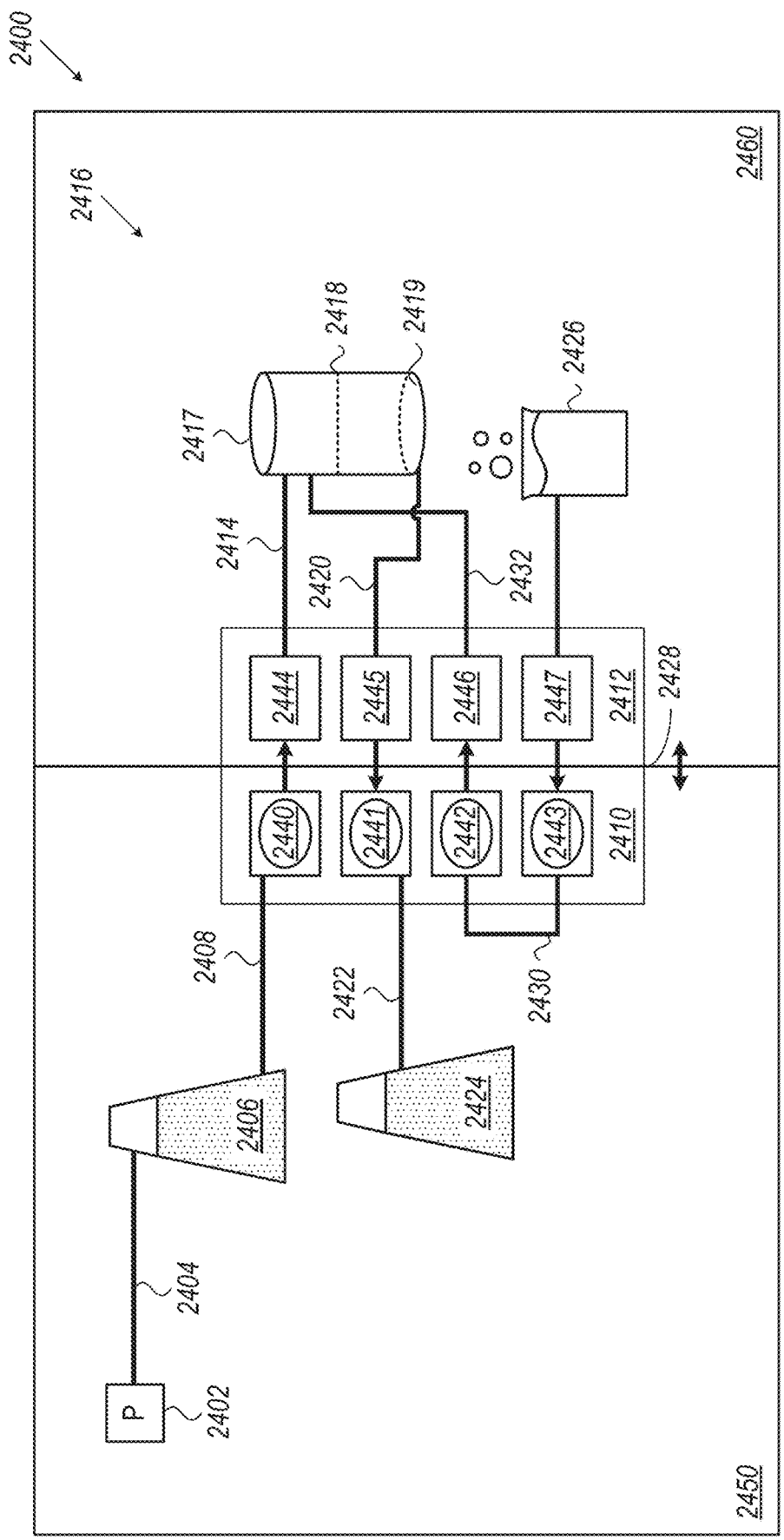
FIG. 24 depicts a schema of a system for biochemical purification, in accordance with the principles of the described embodiments.

FIG. 24 depicts a schema of a system 2400 for biochemical purification (or "downstream system"), in accordance with principles of the disclosure. System 2400 may include a first compartment 2450 and a second compartment 2460, which are reversibly connectable to one another (indicated by double-headed arrows) at interface 2428. Pressure actuator 2402 is configured to transmit pressure via gas conduit 2404 to first sample container 2406, causing sample (indicated by gray shading) to move via first sample conduit 2408 to first connector 2440, which connects to fifth connector 2444, which connects to upstream end 2417 of fractionation moiety 2416, which is located within second compartment 2460. Connection between fifth connector 2444 and fractionation moiety 2416 may be either direct or via optional first additional sample line 2414. Pressure from actuator 2402 may move sample from upstream end 2417 to downstream end 2419 of fractionation moiety 2416. Fractionation moiety 2416 may optionally include filter 2418. Pressure from actuator 2402 may move sample from downstream end 2419 to sixth connector 2445, which connects to second connector 2441, which connects to second sample conduit 2422, which connects to second sample container 2424. Connection between fractionation moiety 2416 and sixth connector 2445 may be either direct or via optional second additional sample line 2420. Second compartment 2460 also contains reagent container 2426, which connects to eighth connector 2447, which connects to fourth connector 2443, which connects to reagent conduit 2430, third connector 2442, seventh connector 2446, and fractionation moiety 2416. Connection between reagent container 2426 and eighth connector 2447 may be either direct or via optional first additional reagent line 2433. Connection between seventh connector 2446 and fractionation moiety 2416 may be either direct or via optional second additional reagent line 2432.

With further reference to FIG. 24, connectors 2440-2443 are located within orifices within interface side 2410 of first compartment 2450. Connectors are depicted as circles, and orifices as unnumbered squares. Connectors 2444-2447 are located within connector manifold 2412 of second compartment 2460.

Figure 25:
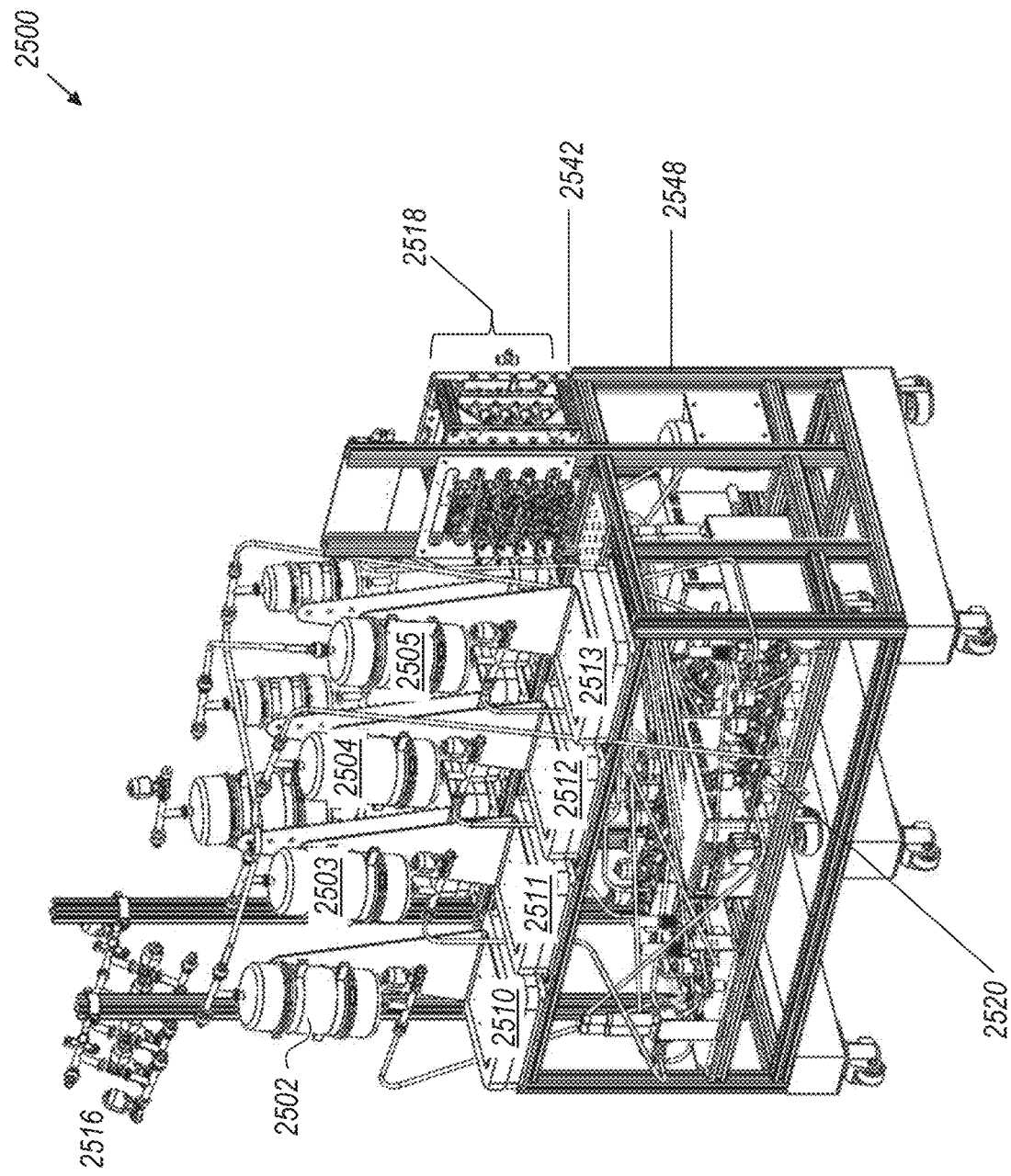
FIG. 25 depicts an oblique view of a compartment of a biochemical purification apparatus, in accordance with the principles of the described embodiments.

FIG. 25 shows an oblique view of first compartment 2500 of a biochemical purification (or "downstream") apparatus, in accordance with principles of the disclosure. Seven tanks are present, with 4 tanks, numbered 2502-2505, fully visible in this view. Tanks 2502-2505 are suspended on L-shaped mounting plates (see FIG. 4), which rest on scales 2510-2513, respectively. As fluid is added or samples are removed from a tank, its mass will change, from which the flow rate and mass transfer can be deduced Also shown are utility distribution manifold 2516, which can be used to route pressurized air, steam, and cleaning fluid, and fluid diversion/outlet valve manifold 2520. Also shown is an oblique view of the side of connection interface 2518. Scales 2510-2513, connection interface 2518, and associated apparatus are attached to and supported by rigid baseplate 2542. Depicted components are attached to, organized, and supported by rigid frame 2548. Connection interface 2518 serves to connect first component to second component (not shown).

Figure 26:
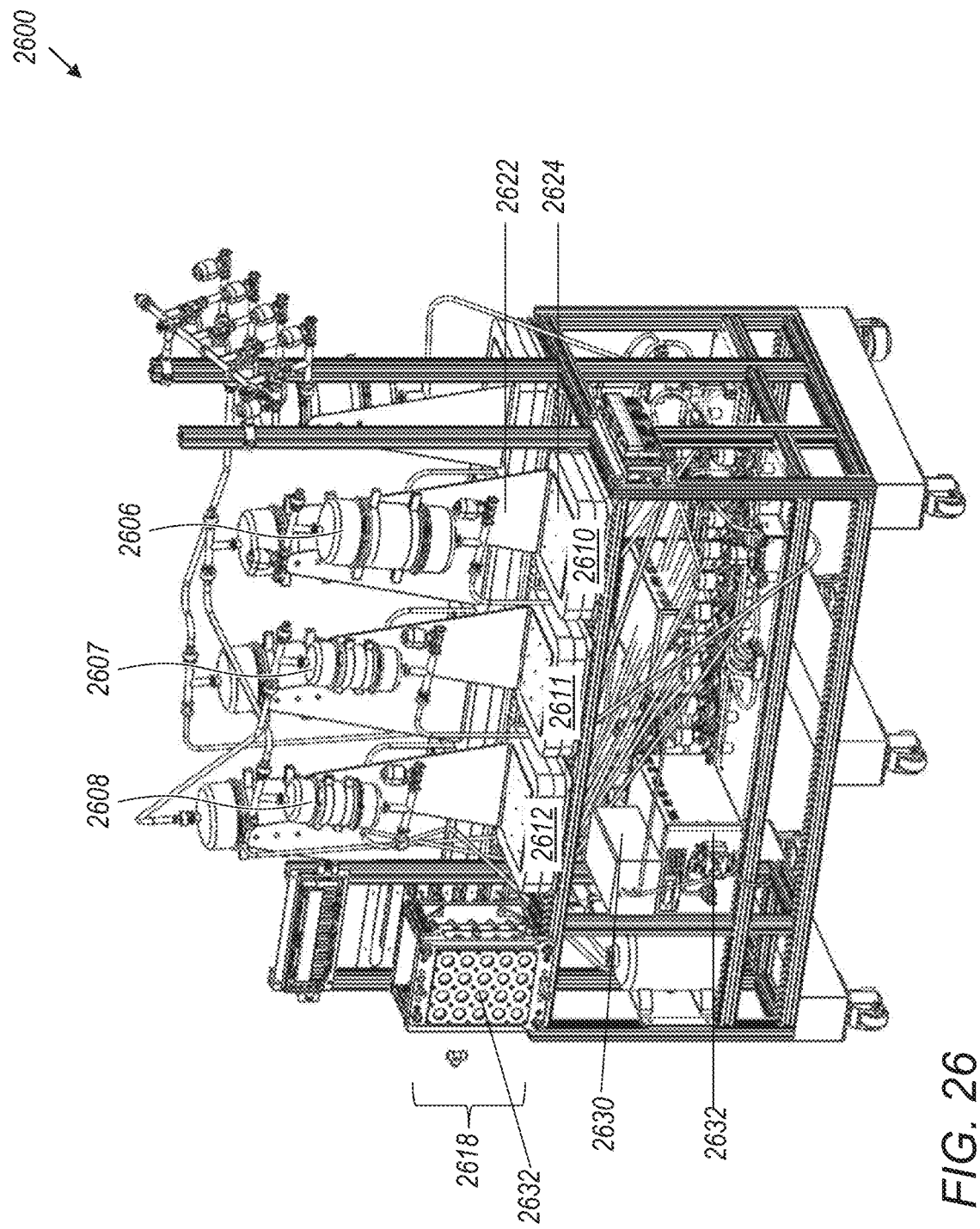
FIG. 26 depicts an oblique view of a compartment of a biochemical purification apparatus, in accordance with the principles of the described embodiments.

FIG. 26 shows an oblique view of first compartment 2600 of a biochemical purification apparatus, in accordance with principles of the disclosure. View is rotated nearly 180 degrees in a horizontal plane, relative to FIG. 25, providing an unobscured view of the remaining 3 tanks, 2606-2608. This view also provides an oblique, nearly frontal view of steam manifold block 2632 on connection interface 2618. Tanks 2606-2608 are suspended on L-shaped mounting plates 2622, with the bottom section 2624 of each mounting plate resting on one of scales 2610-2612, respectively. Inline degasser 2630 and pulseless constant flow pump 2632 are also depicted.

Figure 27:
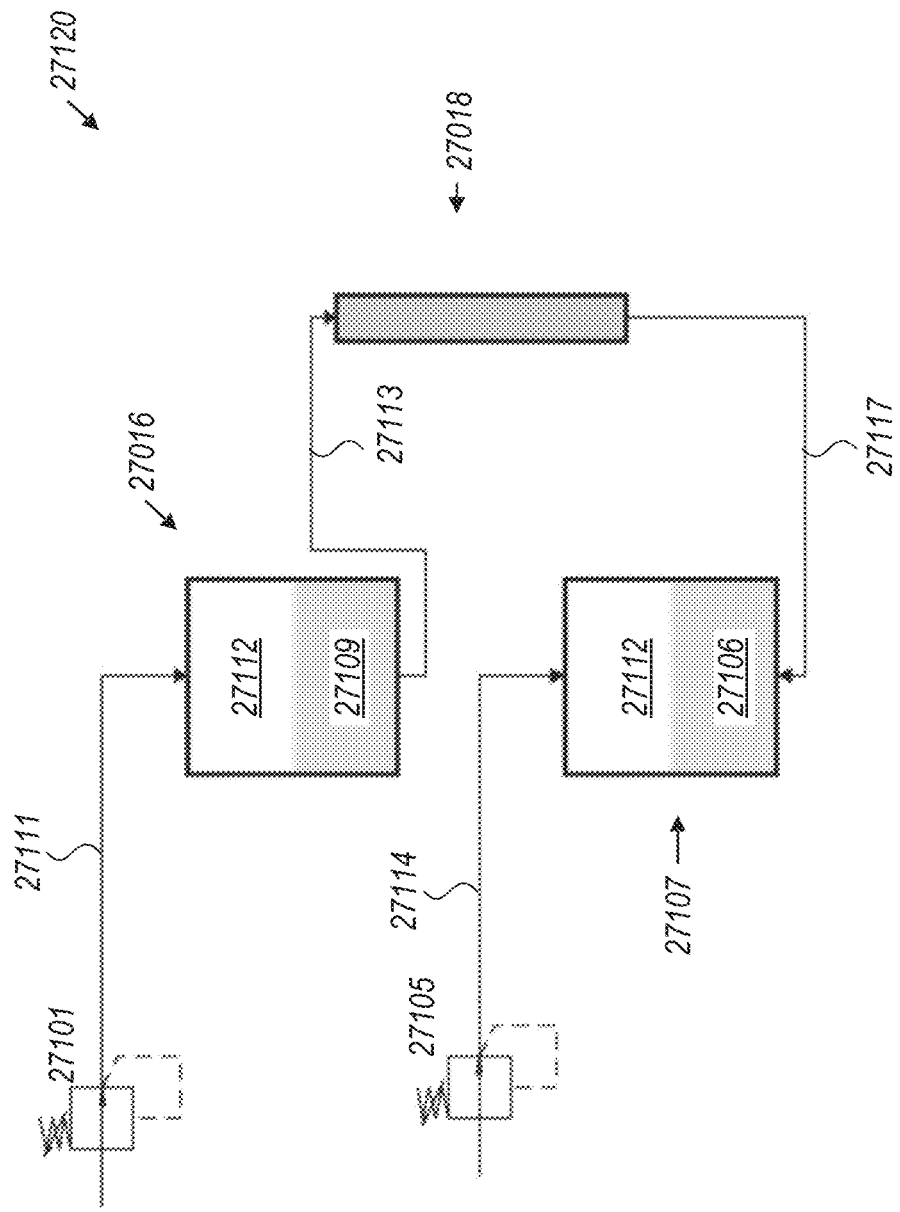
FIG. 27 is a schematic depiction of a described fluid propulsion system, in accordance with the principles of the described embodiments.

FIG. 27 is a schematic depiction of a system 27120, in accordance with principles of the disclosure, for bidirectionally impelling a sample out of tanks and across a separation moiety 27018, in accordance with principles of the disclosure. First pressure actuator 27101, which may be a pressure regulator, may be programmatically set to a predetermined pressure level by a controller (not depicted). If the pressure level is greater than the pressure in the proximal air line 27111, which is disposed downstream relative to first actuator 27101, then pressured air flows through the proximal air line. Pressurized air proceeds through air line 27111 to headspace 27112 of first sample container 27016. Increased pressure in headspace 27112 impels sample 27109 out of container 27016, through downstream fluid line 27113, into separation moiety 27018.

To reverse flow of fluid through separation moiety 27018, second pressure actuator 27105, which may be a pressure regulator, is set to a pressure level by a controller. First pressure actuator may be switched to passive (venting) mode or set to a lower pressure than second pressure actuator. Pressurized air is impelled through second proximal air line 27114, into headspace 27112 of second sample container 27107, impelling sample 27106 through second downstream fluid line 27117 into separation moiety 27018.

Alternating, two-way movement of fluid back and forth through separation moiety 27018 may be performed by alternating higher pressures between pressure actuators 27101 and 27105.

One of ordinary skill in the art will appreciate that the steps shown and described herein may be performed in other than the recited order and that one or more steps illustrated may be optional.

Thus, methods, systems, and apparatuses products may improve and optimize biotechnological processes, such as cell culture and downstream purification steps. Persons skilled in the art will appreciate that the present invention can be practiced by other than the described embodiments, which are presented for purposes of illustration rather than of limitation.

What is claimed is:

1. A system, the system comprising a first and second conduit, the first and second conduit being at least partially disposed in a first compartment and a second compartment, respectively, wherein:
   the first compartment comprises a block and a surface perforation, the perforation opening into a cavity in the block;
   the cavity houses an intracavitary cannular protrusion;
   the intracavitary cannular protrusion is fluidly connected to the first conduit;
   the second compartment comprises a surface cannular protrusion protruding therefrom;
   the surface cannular protrusion is fluidly connected to the second conduit;
   the second compartment is configured to be pressed against the first compartment, so as to form a steam-tight chamber partially bounded by the cavity, wherein:
     the chamber houses the intracavitary cannular protrusion and the surface cannular protrusion; and
     in a first configuration, the intracavitary cannular protrusion and the surface cannular protrusion axially align with one another without contacting one another,
     and the intracavitary cannular protrusion and the surface cannular protrusion are each configured to automatically shut off liquid flow therethrough;
   the chamber is at least partially surrounded by a cooling channel connected to a liquid channel;
   the system comprises a waterproof boundary between the chamber and the cooling channel;
   the chamber comprises a steam inlet opening, wherein the steam inlet opening is connected to a steam channel that traverses the cooling channel; and
   in a second configuration, the intracavitary cannular protrusion and the surface cannular protrusion mate with one another, thereby forming a fluid-tight connection; and the system is configured to transition from the first configuration to the second configuration in response to a linear force being exerted on the intracavitary cannular protrusion.

2. The system of claim 1, wherein the block is a contiguous block, the block having a thermal conductivity value at 25° C. of at least 10 W/m*K (Watts per meter Kelvin).

3. The system of claim 1, wherein the cooling channel shares a common wall with the chamber.

4. The system of claim 1, wherein the first compartment contains a single intracavitary cannular protrusion, and the second compartment contains a single surface cannular protrusion.

5. The system of claim 1, wherein the first compartment contains two intracavitary cannular protrusions, and the second compartment contains two surface cannular protrusions.

6. The system of claim 1,
   further comprising a connector having a substantially circular cross section located within the block;
   wherein the connector is operably connected to a linear actuator, the linear actuator being configured to exert the linear force on the intracavitary cannular protrusion via the connector.

7. The system of claim 6, wherein:
   the connector comprises a distal end, the distal end having a depression;
   the first conduit comprises a flange on at least one end; and
   the flange fits into the depression.

8. The system of claim 7, the system further comprising a rigid, perforated disk; and a retaining piece, wherein:
   the disk fits into the depression;
   the retaining piece fits over the distal end of the connector; and
   the retaining piece attaches reversibly to the connector and exerts axial pressure on the disk.

9. A method for sterile fluid transfer between a first conduit and a second conduit, the method comprising:
   juxtaposing a first compartment to a second compartment, wherein:
     the first compartment comprises a block, the block having a first planar face, the first planar face comprising an opening, the opening leading to a cavity, the cavity located within the block;
     a first cannular protrusion is disposed in the cavity;
     the cavity is at least partially surrounded by a cooling channel connected to a liquid channel, wherein the chamber is fluidly insulated from the cooling channel;
     the first cannular protrusion is fluidically connected to the first conduit;
     the second compartment comprises a second planar face, the second planar face comprising a second cannular protrusion, wherein the second cannular protrusion protrudes from the second planar face;
     the second cannular protrusion is fluidically connected to the second conduit; and
     when the planar faces of the first and second compartments are juxtaposed:

the second planar face presses against the opening to form an airtight chamber, wherein the chamber houses the first and second cannular protrusions and is partially bounded by the cavity; and the first and second cannular protrusions axially align without initially contacting one another, and the first and second cannular protrusions do not initially allow liquid flow therethrough;

introducing a heated gas into the chamber via a gas channel that traverses the cooling channel;

removing the gas;

introducing a liquid into the cooling channel;

exerting a linear force on the first cannular protrusion, thereby moving the first cannular protrusion towards the second cannular protrusion, mating the first and second cannular protrusions, and forming a fluidic connection with the second cannular protrusion; and moving a fluid between lumens of the first and second conduits.

10. The method of claim 9, wherein the second cannular protrusion is surrounded by a sealing surface, wherein the sealing surface presses against the opening to form the airtight chamber.

\* \* \* \* \*